United States Patent [19]
Ghadiri

[11] Patent Number: 5,408,036
[45] Date of Patent: Apr. 18, 1995

[54] ISOLATED METALLOPOLYPEPTIDE: COMPOSITIONS AND SYNTHETIC METHODS

[75] Inventor: M. Reza Ghadiri, Del Mar, Calif.

[73] Assignee: The Scripps Research Institute, La Jolla, Calif.

[21] Appl. No.: 164,618

[22] Filed: Dec. 9, 1993

Related U.S. Application Data

[63] Continuation of Ser. No. 769,621, Sep. 23, 1991, abandoned, which is a continuation-in-part of Ser. No. 591,988, Oct. 2, 1990, Pat. No. 5,200,504.

[51] Int. Cl.$^6$ .................... A61K 37/02; A61K 37/26; C07K 5/00; C07K 7/00
[52] U.S. Cl. ................................. 530/304; 530/300; 530/326
[58] Field of Search ............... 530/326, 300, 304

[56] References Cited

U.S. PATENT DOCUMENTS 4,849,505  7/1989  Stavrianopoulos ............... 530/300

OTHER PUBLICATIONS

Anderson et al., *Inorganic Chemistry*, vol. 25 No. 27, pp. 4847–4851, 1986.
J. Berg., *Proc. Natl. Acad. Sci.*, vol. 85, pp. 99–102, 1988.
Kemp et al., *Tetrahedron Lett.*, vol. 29, pp. 4931–4934, 1988.
Ghadiri et al, *J. Am. Chem. Soc.*, vol. 112, pp. 9633–9635, 1990.
Ghadiri et al., "Peptide Architecture. Design of Stable α–Helical Metallopeptides via a Novel Exchange–Inert Ru$^{III}$ Complex", *J. Am. Chem. Soc.*, 112:9633–9635 (1990).
Schiffer et al., "Use of Helical Wheels to Represent the Structures of Proteins and to Identify Segments with Helical Potential", *Biophysical Journal*, 7:121–135 (1967).
International Search Report, PCT/US91/07248.
Kemp et al., *Tetrahedron Lett.*, 29(39):4931–4934 (1988).
Tainer et al., *Nature*, 306:284–287 (1983).
Felix et al., *J. Pep. Prot. Res.*, 32:441–454 (1988).
Ghadiri et al., "Approaches Toward Total Synthesis of Artificial Receptors and Proteins", *Scientific Report 1988–89*, vol. 15 of the Research Institute of Scripps Clinic, p. 35.
Ghadiri et al., "Design and Synthesis of Artificial Proteins, Receptors, and Enzymes", *Scientific Report 1989–90*, vol. 16 of the Research Institute of Scripps Clinic, pp. 172–173.
Ghadiri et al., "Secondary Structure Nucleation in Peptides. Transition Metal Ion Stabilized α–Helics", *J. Am. Chem. Soc.*, 112:1630–1632 (1990).

Primary Examiner—Robert J. Hill, Jr.
Assistant Examiner—A. M. Davenport
Attorney, Agent, or Firm—Welsh & Katz, Ltd.

[57] ABSTRACT

This invention contemplates an isolated metallopolypeptide comprising a polyvalent metal ion coordinately linked to 2 to about 8 polypeptide binding ligands, wherein at least 2 of said polypeptide binding ligands are covalently bonded to a linear amphiphilic peptide. The linear amphiphilic peptide has an alpha-helix, beta-sheet or beta-turn conformation. This invention further contemplates a metal ion-assisted, self-assembly method for producing a metallopolypeptide.

5 Claims, 8 Drawing Sheets

ISOLATED METALLOPOLYPEPTIDE: COMPOSITIONS AND SYNTHETIC METHODS

CROSS-REFERENCE TO APPLICATION

This application is a continuation of application Ser. No. 07/769,621, filed Sep. 23, 1991, and now abandoned, which is a continuation-in-part of U.S. patent application Ser. No. 07/591,988 filed Oct. 2, 1990, and now U.S. Pat. No. 5,200,504.

TECHNICAL FIELD OF THE INVENTION

This invention relates to an isolated metallopolypeptide and a metal-ion assisted self-assembly method for synthesizing such a metallopolypeptide.

BACKGROUND OF THE INVENTION

Natural proteins are made up of linear chains of amino acid residues linked by amide bonds. The polypeptide chain is flexible and has virtually complete conformational freedom. Despite this freedom, natural polypeptides adopt tightly packed, highly ordered folded structures such as alpha-helices, beta-sheets and beta-turns, i.e., form non-random secondary structures. The energy balance between folded and unfolded states of polypeptides is thought to be regulated by conformational entropy factors. One such factor, the hydrophobic effect, is now thought to be the major driving force in protein folding. Dill, K. A., *Biochemistry*, 24:1501 (1985).

When two or more hydrophobic groups (initially solvated by a highly ordered water shell) clump together in the interior of a protein, the increase in the solvent entropy is more than compensated for by the loss of conformational entropy accompanying this event. The interaction of the polypeptide with the solvent surroundings causes non-polar side chains to cluster together in the interior and the hydrophilic groups to remain largely at the protein surface. According to one theory, the hydrophilic interactions force rapid collapse of the polypeptide to a compact state called the "molten globule", which then rearranges the final structure. See. e.g., Pain, R., *Trends Biochem. Sci. Pers. Ed.*, 12:309 (1987); Dolgikh et al., *FEBS Lett.*, 136.311 (1981); and Kuwajima et al., *FEBS Lett.*, 221:115 (1987).

Folded structures such as alpha helices and beta sheets are maintained by an extensive hydrogen bond network. Richardson, J. S., *Adv. Protein Chem.*, 34:167 (1981). Although the contribution of a single such hydrogen bond is typically very small, the cooperative formation of hydrogen bonds, particularly in the interior of a protein, likely plays an important role in folding and stability. Other forces contributing to the stability of folded polypeptides are electrostatic forces, medium and long-range ion-pairing interactions, helix-dipole interactions, covalent forces such as disulfide bonding and the nature of C- and N-termini amino acid residues. See, e.g., Barlow et al., *J. Molec. Biol.*, 168:867 (1983); Perutz, M. F., *Science*, 201:1187 (1978); Richardson et al., *Science*, 240:1648 (1988); and Presta et al., *Science*, 240:1632 (1988). Dispersion forces and van der Waal's forces are likely less important in this regard.

Despite the accumulation of a large body of information about folded protein structures, the de novo design of artificial polypeptides having a defined conformation remains an elusive task. The major obstacle in the design of such polypeptides from linear polypeptide sequences is the lack of any comprehensive understanding of how the one-dimensional sequence information directs the formation of a discrete three-dimensional state (topology) of a polypeptide.

Two types of approaches, biometric and nonlinear, have been recently reported and utilized for the de novo design of polypeptides. See, e.g., Richardson et al., *Trends Biochem. Sci.*, 14:304 (1989); and Mutter et al., *Agnew. Chem. Int. Ed. Engl.*, 5:535 (1989). The biometric design approach attempts to model the natural shape and structure of proteins by designing linear peptide sequences that are predicted to fold into a desired topology. For example, recombinant DNA technologies have been used to design and construct a synthetic polypeptide having an anti-parallel tetra-helical topology. See, e.g., Hecht et al., *Science*, 249:884 (1990); and Regan et al., *Science*, 241:976 (1988). A tri-helical peptide has recently been described. Lieberman et al., *J. Am. Chem. Soc.*, 113:1470 (1991).

Other attempts to design and construct synthetic polypeptides having a desired topology have been hampered by a number of problems. A beta-barrel protein called "b-bellin" has been designed but its structural characteristics remain unknown because of solubility problems. Richardson et al., *Trends Biochem. Sci.*, 14:304 (1989). Similar solubility problems have been encountered with synthetic polypeptides having combined beta- and alpha-helical topologies.

Some problems have been avoided by the use of nonlinear design principles. Using a template-assisted approach, several alpha-helical and beta-strand polypeptides comprising identical amphiphilic peptides have been designed. See, e.g., Sasaki et al., *J. Am. Chem. Soc.*, 111:380 (1989); and Hahn et al., *Science*, 248:1544 (1990). The topology of these polypeptides, however, has not yet been fully elucidated.

One approach for the construction of artificial polypeptides having a defined topology is to develop self-organizing molecular processes by which small peptides can be assembled into large and topologically predetermined polypeptide tertiary structures.

The present invention provides a polyvalent metal ion-assisted self-assembly process for the construction of artificial polypeptides in which the overall topology of the polypeptide is manipulated by exploiting the interaction of a polyvalent metal ion with an appropriately designed metal ion binding site.

SUMMARY OF THE INVENTION

The present invention provides an isolated metallopolypeptide comprising a polyvalent metal ion coordinately linked to 2 to about 8 polypeptide binding ligands, wherein at least 2 of said polypeptide binding ligands are covalently bonded to a linear amphiphilic peptide.

A preferred polyvalent metal ion is Ni, Cu, Fe, Co, Ru, Rh, Pd or Pt. A polypeptide binding ligand used in this method is preferably a derivative of pyridine or imidazole such as 2-carboxylpyridine, 3-carboxylpyridine, 5-carboxyl-2,2'-bipyridine or an N—$C_1$–$C_5$ alkyl-carboxy imidazole, such as N-5-carboxypentanyl imidazole.

The linear amphiphilic peptides used to synthesize a metallopolypeptide have an alpha-helical, beta-sheet or beta-turn conformation in solution. In one embodiment, such a linear amphiphilic peptide is a metallopeptide.

The polypeptide binding ligand can be bonded to a linear amphiphilic peptide at any point along the length of the peptide. Preferably, such bonding occurs at the N-terminus of the linear amphiphilic peptide.

The present invention further provides a parallel tetra-helical metallopolypeptide comprising a polyvalent metal ion coordinately linked to 4 polypeptide binding ligands, each of which polypeptide binding ligands is independently covalently bonded to a linear amphiphilic peptide having the formula, reading from left to right in the direction from the N-terminus to the C-terminus:

-Gly-Leu-Ala-Gln-Lys-Leu-Leu-Glu-Ala-Leu-Gln-
Lys-Ala-Leu-Ala-CONH$_2$ (SEQ ID NO:1).

In a preferred embodiment, the polyvalent metal ion is Ru and the polypeptide binding ligand is 3-carboxyl-pyridine.

The present invention also provides a tri-helical metallopolypeptide comprising a polyvalent metal ion coordinately linked to three 5-carboxyl-2,2'-bipyridine polypeptide binding ligands, each of which polypeptide binding ligands is independently covalently bonded to a linear amphiphilic peptide having the formula, reading from left to right in the direction from the N-terminus to the C-terminus:

-Gly-Glu-Leu-Ala-Glu-Gln-Lys-Leu-Glu-Gln-Ala-
Leu-Gln-Lys-Leu-Ala- (SEQ ID NO:18).

In a preferred embodiment, the polyvalent metal ion is Ni, Co, Fe, or Ru.

The tetra- and tri-helical metallopolypeptides have use as oxidation-reduction enzymes and transmembrane charge transfer entities.

The present invention still further provides a metal ion-assisted, self-assembly method comprising the steps of:
  a) providing an isolated peptide-ligand conjugate whose peptide portion is a linear amphiphilic peptide and whose ligand portion is a binding ligand that forms a polypeptide coordination complex with a water-soluble polyvalent metal ion having 2 to 8 coordination sites;
  b) admixing an excess of said peptide-ligand conjugate in a liquid medium with said water-soluble polyvalent metal ion to form a reaction mixture, said excess referring to the moles of said peptide-ligand conjugate over the moles of said polyvalent metal ion coordination sites; and
  c) maintaining said reaction mixture for a time period and under conditions sufficient for said peptide-ligand conjugate and said polyvalent metal ion to form a metallopolypeptide having 2 to 8 linear amphiphilic peptides.

In a preferred embodiment, the linear amphiphilic peptide forms an alpha-helix in solution; the polypeptide coordination complex has a C4 symmetry, an octahedral or square planar geometry and is complexed to 4 peptide-ligand conjugates; and the metallopolypeptide has a parallel tetra-helical topology.

A preferred polypeptide coordination complex having a C4 symmetry and an octahedral or square planar geometry has the formula: trans-[M(L)$_4$(Cl$_2$)$_n$], where L is 3-carboxylpyridine or N-substituted imidazole, M is Ni, Cu, Co, Rh, Ru, Pd or Pt, and n=0 or 1 with the proviso that when M is Pd or Pt, n=0. In a preferred embodiment, M is Ru and n=1.

In another preferred embodiment, the linear amphiphilic peptide forms an alpha-helix in solution; the polypeptide coordination complex has a C3 symmetry, an octahedral or square planar geometry and is complexed to 3 peptide-ligand conjugates; and the metallopolypeptide has a tri-helical topology.

An alternative metal ion-assisted, self-assembly method comprises the steps of:
  a) providing a polypeptide coordination complex having a water-soluble polyvalent metal ion with 2 to 8 coordination sites linked to 2 to 8 polypeptide binding ligands;
  b) admixing said polypeptide coordination complex with an excess of a linear amphiphilic peptide to form a reaction mixture, said excess referring to the moles of said linear amphiphilic peptide over the moles of said polypeptide coordination complex; and
  c) maintaining said reaction mixture for a time period and under conditions sufficient for said polypeptide coordination complex and said linear amphiphilic peptide to form a metallopolypeptide having 2 to 8 linear amphiphilic peptides.

BRIEF DESCRIPTION OF THE DRAWINGS

In the drawings, which form a portion of this disclosure.

In Figure A, the CD spectrum of peptide SEQ ID NO:2 (Table 2) is shown ($5.9 \times 10^{-6}$M in 10 mM sodium borate, 0.5 mM mercaptoethanol, pH 8.0, 21° C.) in the presence of increasing amounts of CdCl$_2$. From the top curve (arrow) to the bottom curve, the Cd$^{2+}$ concentrations shown include 0, $10 \times 10^{-5}$, $2.5 \times 10^{-5}$, $4.0 \times 10^{-5}$, and $1.5 \times 10^{-4}$M, respectively. The decrease in the CD spectrum value reflects the increased stability of the peptide alpha-helical conformation by increased metal ion concentrations.

In Figure B, the CD spectrum of peptide SEQ ID NO:2 is illustrated at $2.2 \times 10^{-6}$M in water at pH 6.65 and 4° C. (dotted curve), and in $7.3 \times 10^{-4}$M CdCl$_2$ solution, pH 6.7, at 4° C. (solid curve). The presence of a metal ion at 4° C. results in increased alpha-helix stabilization compared to a solution without metal ions.

In Figure C, the CD spectrum of peptide SEQ ID NO:3 is shown ($1.8 \times 10^{-6}$M and 5 mM sodium borate, pH 6.1 at 21° C.) in the presence of the following concentrations of CuSO$_4$ (solid curves): 0, $3$ $3 \times 10^{-5}$, and 6.6×10⁻⁵M (top to bottom). The curves decrease at 220 nm as the metal ion concentration increases. The dashed curve shows the CD spectrum of peptide 2 (1.8×10⁻⁶M) in 5 mM sodium borate, 7.4×10⁻⁵M CuSO$_4$, pH 6.4 at 0° C.

The value of $[\Theta]_{222} \times 10^{-3}$ in CD spectra of metal ion-containing peptide solutions decreases as the concentration of the metal ion increases reflecting increased alpha-helix formation. This property is enhanced in solutions at 0° C.

Figure 4:
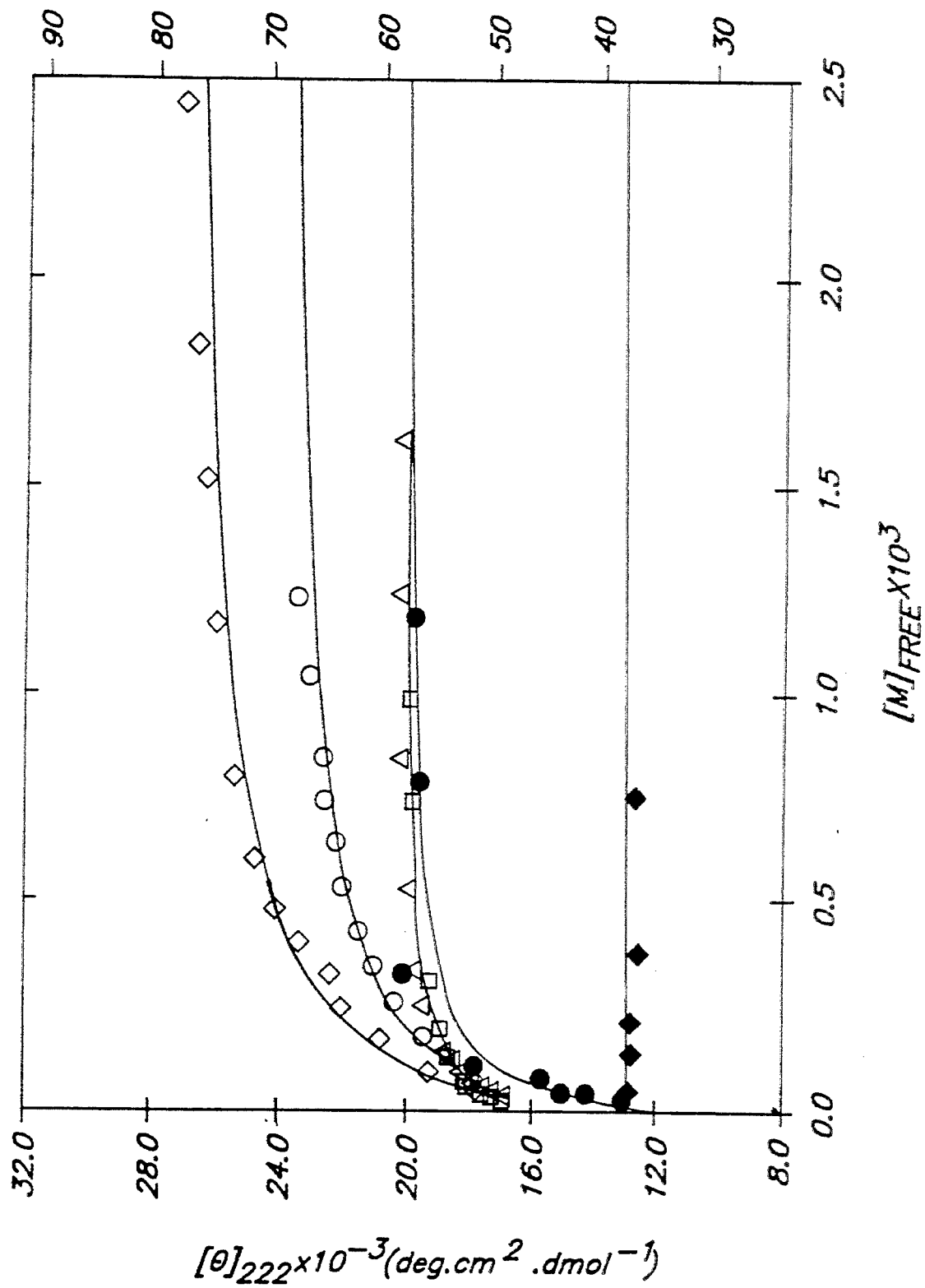

FIG. 4 illustrates the dependence of mean residue molar ellipticity at 222 nm ($[\Theta]_{222} \times 10^{-3}$) of peptides SEQ ID NO's:2 AND 3 on the concentration of free metal ions when measured as described in Example 3A(2). Peptide SEQ ID NO:2 at 5.9×10⁻⁶M in 10 mM sodium borate, 0.5 mM mercaptoethanol, 21° C. was combined with the following metal ions at various concentrations under the indicated conditions and assays (closed circles) CdCl$_2$, pH 8.0, $K_d$=5.6×10⁻⁵M; (closed diamonds) ZnCl$_2$ pH 8.0. Peptide SEQ ID NO:3 at (6.1×10⁻⁵M in 5 mM sodium borate, 21° C. was similarly combined and assayed: (open triangles) ZnCl$_2$, pH 7.5 $K_d$=7.5×10⁻⁵M; (open squares) CuCl$_2$, pH 5.3, $K_d$=6.6×10⁻⁵M; (open circles) CdCl$_2$, pH 7.5 $K_d$=2.2×10⁻⁴M; (open diamonds) NiCl$_2$, pH 6.3 $K_d$=2.1×10⁻⁴M. The curves were fit to the data by using nonlinear least-squares method. The results indicate that metal ions have different affinities depending on the metal binding site in the synthetic peptide. NiCl$_2$ exhibited the highest affinity followed by CdCl$_2$ for peptide SEQ ID NO:3. CdCl$_2$ exhibited a greater affinity for peptide SEQ ID NO:2 than CdCl$_2$.

Figure 5:
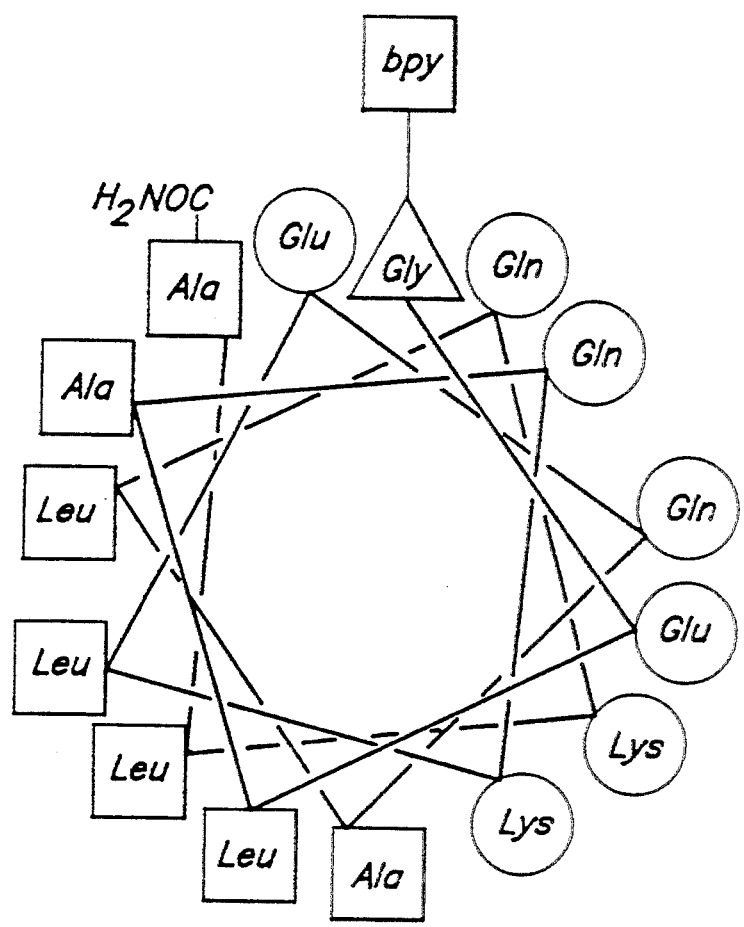

FIG. 5 shows a helical wheel diagram of a linear amphiphilic peptide covalently bonded to a bipyridyl (bpy) polypeptide binding ligand illustrating the segregation of hydrophobic (Ala, Leu) and hydrophilic (Gln, Glu, Lys) residues.

Figure 6:
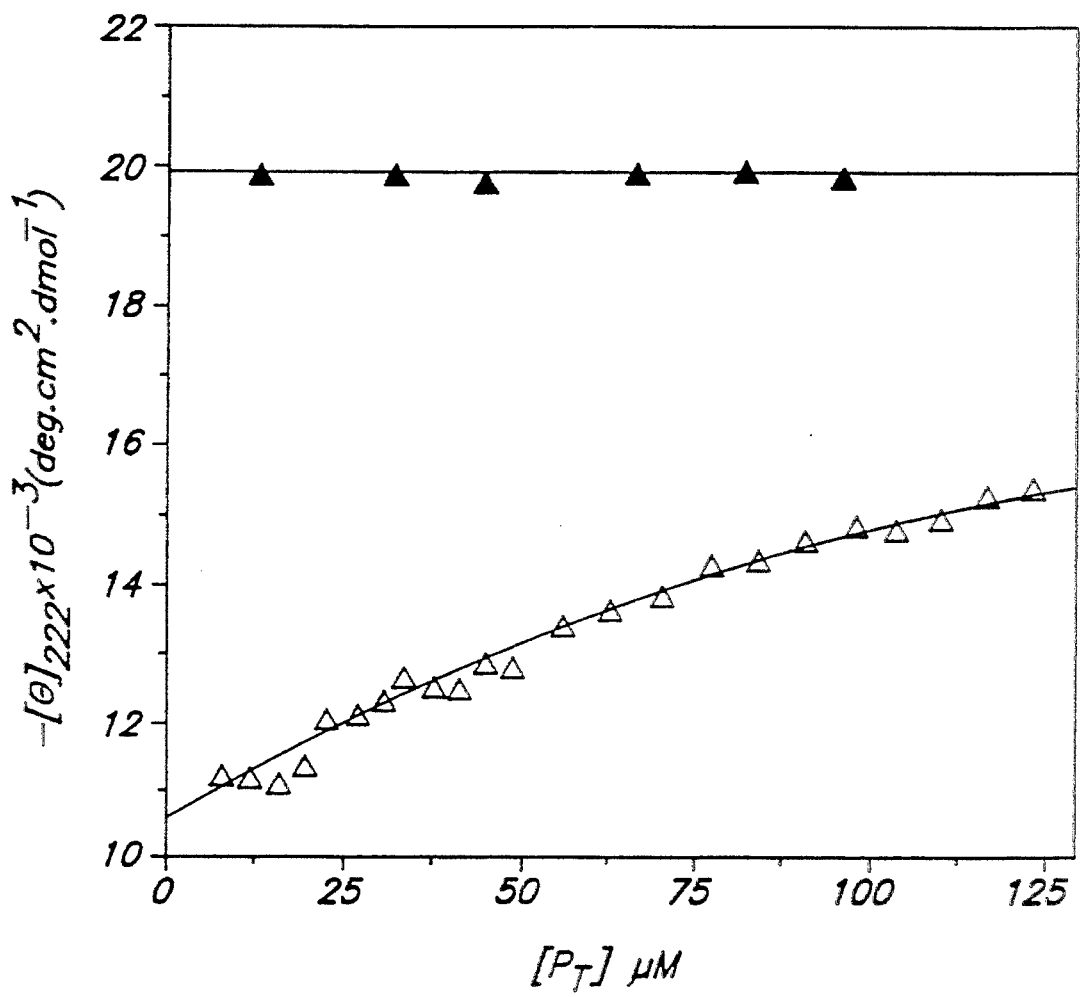

FIG. 6 shows the concentration dependence of the ellipticity of the peptide of Example 4 and of FIG. 5 at 222 nM: (closed triangles), peptide plus 2.5 equivalence of CoCl$_2$; (open triangles), peptide in the absence of added metal ions at various concentrations. Data (Δ) were analyzed according to monomer-ηmer equilibria using the equation below, where $P_n$, $P_{mon}$, and $P_T$ are the self-associated, monomeric, and total concentrations of the peptides, respectively, n is the degree of association, $\theta_{mon}$ is the ellipticity of the monomer, and $\theta_n$ is the ellipticity of the self-associated form of the peptide. The values of n=1.95, $\theta_{mon}$=−10,100, $\theta_n$=−27,900, and $K_{diss}$=6.4×10⁻⁴ were determined by the nonlinear regression program MINSQ.

$$[P_T] = \left\{ \frac{(\theta_{obs} - \theta_{mon})K_{diss}}{n(\theta_n - \theta)(1 - ((\theta_{obs} - \theta_{mon})/(\theta_n - \theta_{mon})))^n} \right\}^{1/(nl)}$$

Figure 7A:
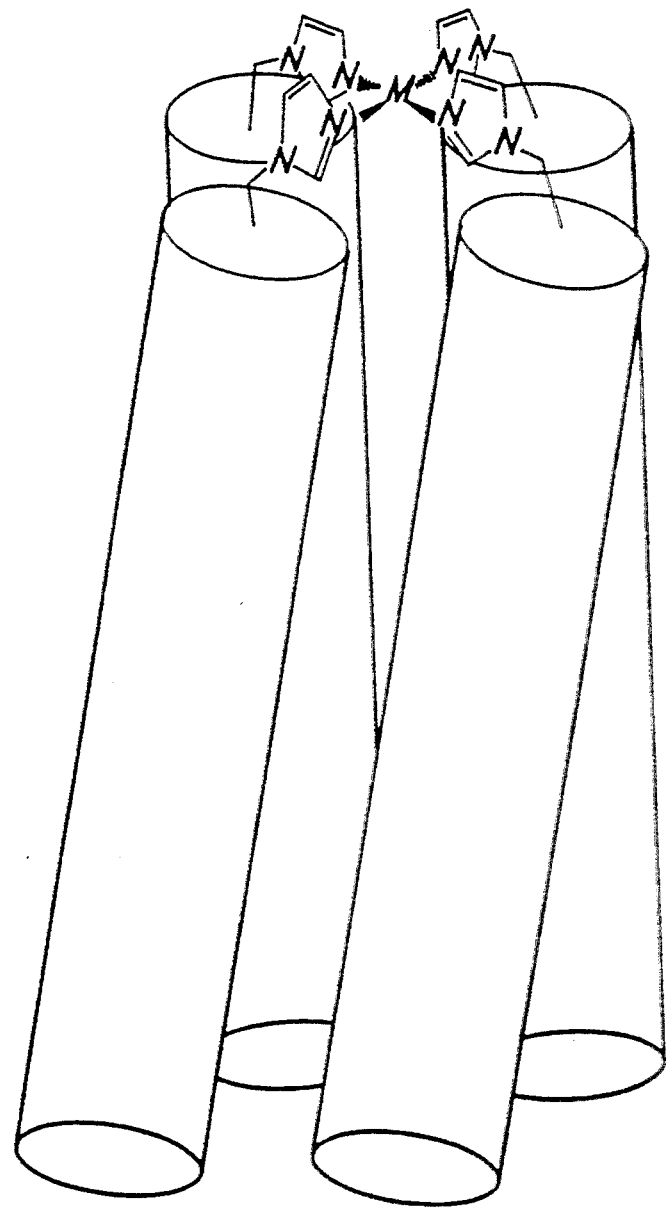
Figure 7B:
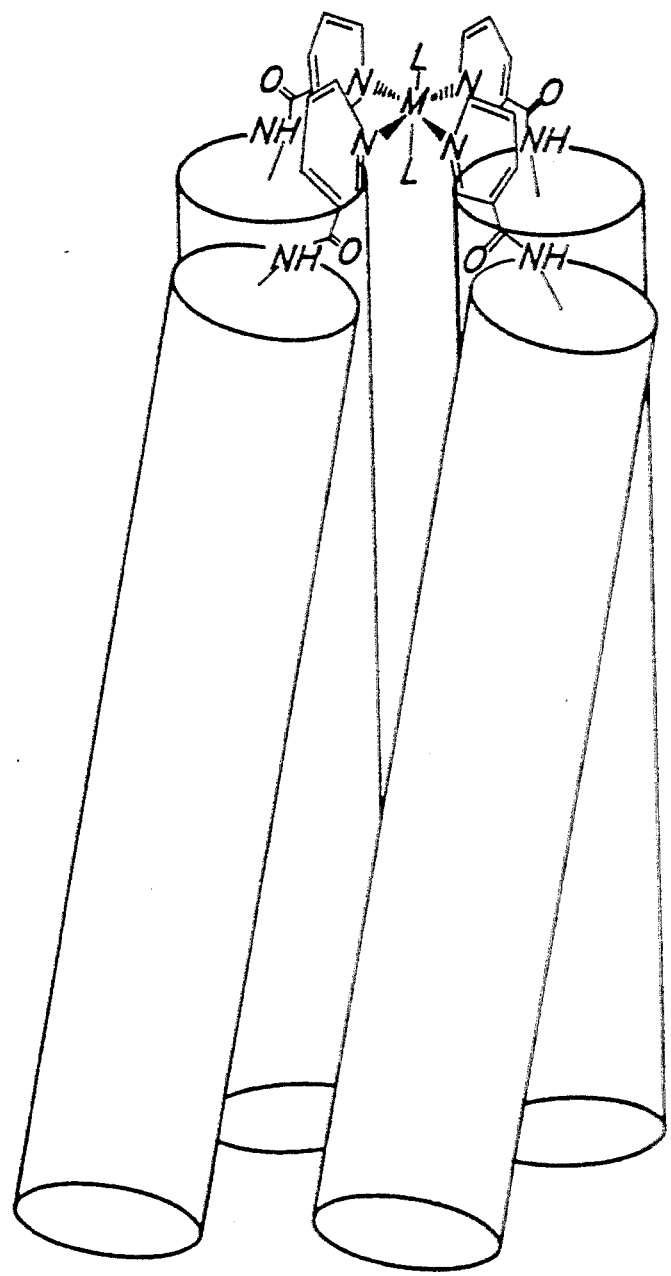

FIGS. 7A and 7B, shown in two panels designated FIGS. 7a and 7b, is a schematic illustration of a parallel tetra-helical metallopolypeptide having a pyridyl (FIG. 7a) or an imidazolyl (FIG. 7b) polypeptide binding ligand.

DETAILED DESCRIPTION OF THE INVENTION

A. Definitions

Amino Acid Residue

The amino acid residues described herein are preferred to be in the "U" isomeric form. However, residues in the "D" isomeric form can be substituted for any L-amino acid residue, as long as the desired functional property is retained by the polypeptide. NH$_2$ refers to the free amino group present at the amino terminus of a polypeptide. COOH refers to the free carboxyl group present at the carboxyl terminus of a polypeptide. Abbreviations for amino acid residues are shown in the following Table of correspondence:

| TABLE OF CORRESPONDENCE | |
|---|---|
| SYMBOL 3-Letter | AMINO ACID |
| Tyr | tyrosine |
| Gly | glycine |
| Phe | phenylalanine |
| Met | methionine |
| Ala | alanine |
| Ser | serine |
| Ile | isoleucine |
| Leu | leucine |
| Thr | threonine |
| Val | valine |
| Pro | proline |
| Lys | lysine |
| His | histidine |
| Gln | glutamine |
| Glu | glutamic acid |
| Trp | tryptophan |
| Arg | arginine |
| Asp | aspartic acid |
| Asn | asparagine |
| Cys | cysteine |
| Xaa | non-naturally occurring amino acid |

It should be noted that all amino acid residue sequences are represented herein by formulae whose left to right orientation is in the conventional direction of amino-terminus to carboxyl-terminus. In addition, the phrase "amino acid residue" is broadly defined to include naturally occurring and non-naturally occurring (unnatural) amino acid structures. Furthermore, it should be noted that a dash at the beginning or end of an amino acid residue sequence indicates a peptide bond to a further sequence of one or more amino acid residues or to a amino-terminal group such as NH$_2$ or acetyl (Ac) or to a carboxyl-terminal group such as COOH or primary amide (CONH$_2$).

Peptide

As used herein, the term "peptide" in all of its grammatical forms including metallopeptide refers to a sequence of amino acid residues connected to one another by peptide bonds between the alpha-amino group and carboxyl group of contiguous amino acid residues. Further, the term "peptide" is used herein to refer to sub-units for the synthesis of a metallopolypeptide.

Polypeptide

As used herein, the term "polypeptide," in all of its grammatical forms including metallopolypeptide, refers to a molecule comprising a plurality of peptides. Although the terms "peptide" and "polypeptide" are sometimes used interchangeably, their meanings herein are not interchangeable.

B. The Invention

I. Metallopolypeptides

In one aspect, the present invention relates to an isolated metallopolypeptide comprising a polyvalent metal ion coordinately linked to 2 to about 8 polypeptide binding ligands, wherein at least 2 of the polypeptide binding ligands are independently covalently bonded to a linear amphiphilic peptide. The remaining coordination sites can be occupied by mono-, di-, tri- or tetra-dentate ligands as are well known in the art. As used herein, the term "isolated" means that the metallopolypeptide is free from other proteins, enzymes, nucleic acids and other like substances.

a. Polyvalent metal ions—Many different metal ions are suitable for use as a polyvalent metal ion in this invention. Preferably, the polyvalent metal ion has 2 to 8 coordination sites and is one that exhibits the greatest stabilization of the metallopolypeptide topology. The capacity of a particular polyvalent metal ion to have a greater stabilizing effect when compared to another polyvalent metal ion is defined by the preference of a polyvalent metal ion for complexing with a particular polypeptide binding ligand. Insofar as the polypeptide binding ligands form a metal binding site, it is such binding ligands, the geometry of such binding ligands, the amphiphilic peptides bonded thereto, and the chemical properties of such binding ligands that create a preference for interaction with a particular polyvalent metal ion. Polypeptide binding ligands are described below in Section Ib.

Stability of a polyvalent metal ion-polypeptide binding ligand complex (hereinafter referred to as a polypeptide coordination complex) in a given metallopolypeptide is a desirable feature of the present invention. Stability of the polypeptide coordination complex is indicated by the conditions under which the polypeptide binding ligand dissociates from the polyvalent metal ion in such a coordination complex. Concomitant with dissociation is a reassociation between the polypeptide binding ligand and either a different or the original polyvalent metal ion.

The process of dissociation and reassociation of a polypeptide coordination complex is referred to as exchange. In relative terms, stable complexes are more exchange-inert and unstable complexes are more exchange-labile. Exchange-inert polypeptide coordination complexes have been previously described and are particularly preferred. For a general discussion of exchange-inert coordination complexes, see Taube, *Chem. Rev.*, 50:69 (1952); Van Wart, *Meth. Enzymol.*, 158:95 (1988); Barton, *Comm. Inorg. Chem.*, 3:321 (1985); "Metal-Ligand Interactions in Organic Chemistry and Biochemistry" Pullman, et al , Eds., D. Reidel, Boston (1977); Margalit, et al., *J. Amer. Chem. Soc.*, 105:301 (1983); and Friedman, et al. *J. Amer. Chem. Soc.*, 112:4960 (1990).

A polyvalent metal ion that forms an exchange-inert polypeptide coordination complex in a metallopolypeptide is preferred over other polyvalent metal ions. The more exchange-inert the polypeptide coordination complex, the higher the melting temperature (Tm) of the metallopolypeptide. Thus, a metallopolypeptide having a relatively exchange-inert polypeptide coordination complex is more thermostable, and thereby imparts on the metallopolypeptide the ability to maintain secondary structures at higher temperatures than a relatively less exchange-inert polypeptide coordination complex.

Exemplary polyvalent metal ions that can be used in the present invention include zinc (Zn), cadmium (Cd), copper (Cu), nickel (Ni), ruthenium (Ru), platinum (Pt), palladium (Pd), cobalt (Co), magnesium (Mg) , barium (Ba), strontium (Sr), iron (Fe), vanadium (V), chromium (Cr), manganese (Mn), rhodium (Rh), silver (Ag), mercury (Hg), molybdenum (Mo) tungsten (W), calcium (Ca), lead (Pb), cerium (Ce), aluminum (Al) and thorium (Th).

The ionic state of the polyvalent metal ions can vary, as is well known. A preferred oxidation or ionic state of a polyvalent metal ion is preferably Zn(II), Cd(II), Cu(I), CU(II), Ni(II), Ru(II), Ru(III), Pt(II), Pd(II), Co(II), Co(III), Mg(II), Ba(II), Sr(II), Fe(II), Fe(III), V(III), Cr(II), Cr(III), Mn(II), Rh(III), Ag(I), Hg(II), (Mo(III), Mo(IV), Mo(V), Mo(VI), W(III), W(IV), W(V), W(VI), Ca(II), Pb(II), Ce(III), Al(III), or Th(IV), where the oxidation state is indicated in parenthesis.

The selection of a particular polyvalent metal ion is also dependent upon the desired topology of the metallopolypeptide. The binding energy of the polypeptide coordination complex and the stringent geometrical requirements present for a metal ion-binding ligand interaction are used to control the oligomeric state as well as the relative orientation of the linear amphiphilic peptides. A polypeptide coordination complex must be utilized that is compatible with the overall topology of the desired metallopolypeptide.

For example, where the isolated metallopolypeptide has a tri-helical coiled-coil topology, preferred polyvalent metal ions are Ni, Co, Fe and Ru (See Example 4 hereinafter).

Alternatively, when the isolated metallopolypeptide has a parallel tetra-helical topology, preferred polyvalent metal ions are Ni, Cu, Co, Rh, Ru, Pd, and Pt. Because of its ability to form an exchange-inert polypeptide coordination complex with the polypeptide binding ligands of the present invention, a more preferred polyvalent metal ion for use in a parallel tetra-helical metallopolypeptide is Ru (See Example 5 hereinafter).

b. Polypeptide Binding Ligands—Polypeptide binding ligands useful in the present invention can have one or more coordinating atoms (i.e., can be unidentate or polydentate). Exemplary unidentate binding ligands include water, ammonia, hydroxide ion, halide ions such as fluoride, chloride, bromide or iodide, monocarboxylate ions containing 1 to about 8 carbon atoms, cyanide ion and the like as are well known in coordination chemistry. Those ligands are usually referred to as aqua, amine, hydroxido, fluoro, chloro, bromo, iodo, monocarboxylato and cyanato, respectively.

Exemplary polydentate ligands include bi-, tri-, and tetra-dentate ligands such as carbonate ion, oxalate ion, 2,2'-bipyridine, 2-substituted pyridine such as 2-carboxylpyridine, 3-substituted pyridine such as 3-carboxylpyridine, ethylenediamine, acetylacetonate ion, 1,10-phenanthroline, 2,2',2"-triaminotriethylamine, triethylenetetramine, ethylenediaminetetracetate ion, imidazole acetic acid, and N-substituted imidazole such as 5-(1-imidazoyl)- pentanoic acid. Those ligands are usually referred to as carbonato, oxalate (ox), 2,2'-bispyridine (bipy), pyridyl (py), ethylenediamine (en), acetylacetonate (acac) 1,10-phenanthroline (phen), 2,2',2"-triaminotriethylamine (tren), triethylenetetramine (trien), ethylenediaminetetraacetato (EDTA), and imidazolyl (im) respectively, with their usually used abbreviations in parentheses. Quinqui-dentate and hexa-dentate ligands are also known.

Preferably, a polypeptide binding ligand effectively competes with water for coordination sites on the metal. The selection of a preferred ligand depends upon the nature of the selected polyvalent metal ion, and vice versa, the selected ion of the polyvalent metal ion depends upon the preferred polypeptide binding ligand.

Other mono-, bi-, tri- and tetra-(quad) dentate ligands are illustrated in Table 1 and still others will be apparent to the skilled practitioner.

TABLE 1

| Binding Ligands | |
|---|---|
| Residue Side Chain[a,b] | Parent Compound |
| 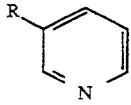 | Pyridine |
| 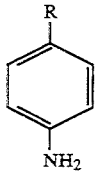 | Aniline |
| 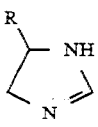 | 3-Azapyrrole |
| 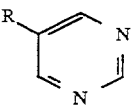 | Pyrimidine |
| 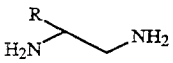 | 1,2-Diaminoethane |
| 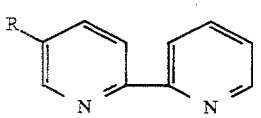 | 2,2'-Bipyridine |
| 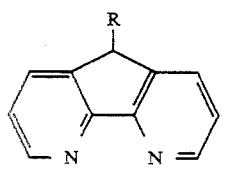 | 6-6'-Methylene bipyridine |
| 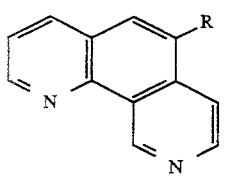 | 1,10-Phenanthroline |
| 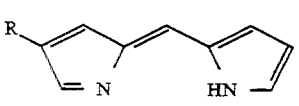 | Hemiporphoryin |
| 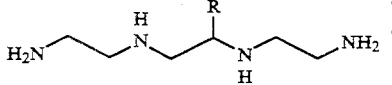 | Triethylenetetramine |
| 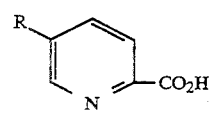 | 2-Carboxylpyridine |

TABLE 1-continued

| Binding Ligands | |
|---|---|
| Residue Side Chain[a,b] | Parent Compound |
| 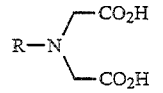 | Amino-diacetic acid |
| R—SH | Hydrogen sulfide |
|  | Mercaptobenzene |
| 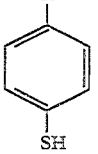 | 1,2-Dimercaptoethane |
| 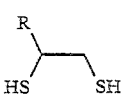 | 2-2'-Bithiophene |
| 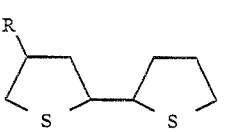 | 2-Carboxylthiophene |

[a] 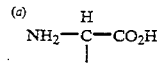 Side Chain

[b] R = Spacer Group, e.g., —(CH$_2$)$_n$—; —C(O)—NH—; —NH—C(O)—

Preferred polypeptide binding ligands are N-substituted imidazole, 3-substituted pyridine, 2-substituted pyridine and bipyridine ligands, as are discussed in detail elsewhere herein.

Generally, the identification of a preferred polypeptide binding ligand for binding a particular polyvalent metal ion can be made by either first selecting the polypeptide binding ligand ion desired to be attached to the linear amphiphilic peptide, then identifying a polyvalent metal ion that binds strongly to that ligand, or the desired polyvalent metal ion can be first identified with preferred peptide binding ligands identified subsequently. Alternatively, polypeptide binding ligands can be screened following identification of a preferred polyvalent metal ion. Such methods of screening are well known to those skilled in the art.

Several well known guiding principles can be used by the skilled artisan in the selection of efficacious polyvalent metal ion-polypeptide binding ligand pairs. Most prominently, preferred metal ion-binding ligand pairs are identified phenomenologically. In this regard, polypeptide binding ligands that coordinately link preferentially to the polyvalent metal ion in the presence of water are preferred. Such binding ligands can be identified by noting the relative binding efficiencies of polyvalent metal ions for such ligands or their analogs in the presence of water.

An example of this principle is illustrated by Ru(NH$_3$)$_5$.(H$_2$O) (ruthenium aquapentamine cation), a polyvalent metal ion well known to fix nitrogen in an aqueous solution. See, H. Taube, et al., J. Am. Chem.

Soc., 89:5706 (1967). Thus, this complex is identified as a likely candidate for coordinate linking to N-lewis base-containing ligands. Similarly, [cis-ruthenium tetraamine]$^{+2}$ is expected to be a good candidate for coordinately linking nitrogen-containing binding ligand bases. Alternatively, polypeptide binding ligands that are good chelators are also preferred candidates.

Another useful screening guideline is related to the Hard-Soft-Acid-Base (HSAB) theory of Pearson as discussed in J. Huheey, *Inorganic Chemistry*, Harper & Row (1972), p.225-35. According to this HSAB theory, "hard acids" have a preferred tendency to bind to "hard bases" whereas "soft acids" have a tendency to bind to "soft bases". Thus, hard acid polyvalent metal ions with high oxidation states have a tendency based on their charge/radius ratios to link to hard base ligands having high charge/radius ratios or to neutral binding ligands having relatively localized electron densities, e.g., hydrated metal ions and electropositive metals. On the other hand, soft acids, such as polyvalent metal ions in their low or zero valance states have a tendency to link to soft binding ligand bases that can accept electron density from the metal, e.g., metal carbonyl, mercaptan and metal-olefin compounds.

The nature of the polypeptide coordination complex (polyvalent metal ion-polypeptide binding ligand complexes) varies with the desired topology of the metallopolypeptide.

Where the isolated metallopolypeptide has a parallel tetra-helical topology, preferred polypeptide coordination complexes are;
  a) labile metal complexes of the type trans-$[M(L)_4Cl_2]$, where for L=3-carboxyl-substituted pyridine, M=Ni(II); and for L=N-substituted imidazole, M=Cu(II), Ni(II), and Co(II); and
  b) exchange-inert complexes such as trans-$[Rh(L)_4Cl_2]^+$, trans-$[Ru(L)_4Cl_2]$, $[Pd(L_4)]^{2+}$, and $[Pt(L_4)]^{2+}$ in which L=a 3-substituted pyridine or an N-substituted imidazole.

These complexes have been extensively characterized and form either square planar (in the case of Pd and Pt complexes) or octahedral complexes with the four ligands occupying the equatorial positions. The C4 symmetry exhibited by such complexes is well-suited for use in the construction of four-equatorial positions and, thus, in the construction of tetra-helical metallopolypeptide. Schematic representations of two embodiments of a parallel tetra-helical metalloprotein are shown in FIGS. 7a and 7b.

The metallopolypeptide comprises four linear amphiphilic peptides having an alpha-helical conformation and terminated by either a pyridyl (FIG. 7a) or imidazolyl (FIG. 7b) polypeptide binding ligand. When the four terminal polypeptide binding ligands coordinate to a metal ion in an octahedral or square planar geometry, the amphiphilic helices come close in space and cluster to form a parallel tetra-helical structure.

c. Linear amphiphilic peptides—At least two of the polypeptide binding ligands are independently covalently bonded to a linear amphiphilic peptide. As used herein, the term "linear amphiphilic peptide" means an amino acid residue sequence comprising an alpha-helical, beta-sheet or beta-turn that, in an aqueous medium, can be divided into separate faces, namely a hydrophobic (non polar) region and hydrophilic (polar), or solvent accessible region. For a comprehensive review of protein structures, see "Prediction of Protein Structure and the Principles of Protein Conformation", Ed. G. D. Fasman, Plenum Press, N.Y. (1989). The word "linear" is used in its sequential sense, rather than to imply that the peptide does not possess a secondary structure or possesses a random secondary structure.

It is understood that a given individual linear amphiphilic peptide can comprise more than one alpha-helix, beta-sheet or beta-turn. Further, a given individual linear amphiphilic peptide can comprise more than one type of linear conformation. Thus, for example, an individual linear amphiphilic peptide of the present invention can comprise one or more alpha-helices, an alpha-helix and a beta-sheet, an alpha-helix, a beta-sheet and a beta-turn, a beta-sheet and a beta-turn and the like. The only limitation on the conformation of an individual linear amphiphilic peptide is that the conformation not adversely interfere with the desired topology of the metallopolypeptide containing such peptide.

Preferably, a linear amphiphilic peptide of the present invention has only one of the conformations set forth above.

Each separate linear amphiphilic peptide of a given metallopolypeptide can have the same or a different conformation. In a preferred embodiment, when the metallopolypeptide comprises 3 or 4 linear amphiphilic peptides, each of the linear amphiphilic peptides has an alpha-helical conformation. As set forth above, the only limitation is that the conformations of the linear amphiphilic peptides do not adversely interfere with the overall topology of the metallopolypeptide.

The linear amphiphilic peptide can contain any number of amino acid residues so long as such peptide has the desired conformation and none of the amino acid residues in the peptide adversely interfere with metallopolypeptide synthesis or topology. Preferably, each linear amphiphilic peptide comprises from 10 to about 200 amino acid residues. More preferably, a linear amphiphilic peptide comprises from 10 to about 40 amino acid residues.

The linear amphiphilic peptide can be a naturally occurring peptide known to have, either wholly or in part, a particular conformation, or a synthetic peptide designed to have a particular conformation in solution.

Exemplary naturally-occurring peptides having wholly or in part an alpha-helical conformation include myohemorythrin, cytochrome B 562, cytochrome C', and Tobacco Mosaic Virus (TMV) coat protein.

Exemplary naturally-occurring peptides having wholly or in part a beta-sheet conformation include the $V_L$ domain of immunoglobulin, domain 2 of pyruvate kinase, superoxide dismutase (SOD), and bovine pancreatic trypsin inhibitor.

Exemplary naturally-occurring peptides having wholly or in part a beta-turn conformation include the $V_L$ domain of immunoglobulin, the flap of human renin (residues 81-90), endothiapepsin (residues 70-85), γ-chymotrypsin A (residues 201-208), and penicillopepsin (residues 198-205 and 237-246).

A naturally-occurring peptide having a known amino acid residue sequence is selected for stabilization of secondary structures. The amino acid residue sequence of the peptide can be obtained from the published literature, from computerized databases, such as GENBANK, the EMBL protein sequence database, and the like well known sources, or can be determined empirically by conducting peptide sequencing or DNA sequencing methods on isolated peptide or cloned DNA, respectively, as is also well known.

The amino acid residue sequence of the selected peptide is then analyzed to identify the presence of regions of amino acid residue sequence capable of forming a secondary structure having a hydrophilic surface (region). These secondary structures include alpha-helices, beta-sheets and beta-turns, as discussed hereinbefore.

A peptide is then prepared according to its known amino acid residue sequence that comprises a sequence of amino acid residues capable of forming a secondary structure as defined herein, namely an alpha-helix, a beta-sheet and a beta-turn, except that amino acid residue substitutions are included in the prepared peptide to provide a pair of coordinating amino acid residues that form a metal binding site.

Alternatively, non-naturally occurring linear amphiphilic peptides can be designed and synthesized to form an alpha-helical, beta-sheet or beta-turn conformation in solution using design principles and synthetic methods well known to those of skill in the peptide synthesis art.

Alpha-helices contain about 3.6 amino acid residues per helical turn. Hydrophobic and hydrophilic amino acid residues are spaced along the linear sequence of the peptide such that when the peptide assumes the alpha-helical conformation, the hydrophobic and hydrophilic amino acid residues are respectively segregated to separate faces of the helix. The segregation of hydrophobic and hydrophilic amino acid residues in an alpha-helix can be visualized in a helical wheel as described in Schiffer et al., *Biophysical J.*, 7:121 (1987), and illustrated hypothetically below.

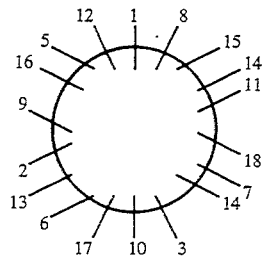

Given that there are 3.6 residues per helical turn, the 18 residue sequence shown above comprises 5 such turns. In such a peptide, the hydrophobic amino acid residues can, for example, be segregated to that face of the helix comprising residue position numbers 6 17, 10, 3, 14, 7, 18 and 11. The hydrophilic residues of this peptide are segregated to that face of the helix comprising, for example, residue positions 15, 8, 1, 12, 5, 16 and 9. The extent of hydrophobicity or hydrophilicity can be altered by varying both the number and character of specific amino acid residues.

Certain hydrophobic and hydrophilic amino acid residues are preferred in constructing alpha-helical peptides. Preferred naturally occurring hydrophobic amino acid residues are Leu, Ala, Ile, Val and Phe. Preferred naturally occurring hydrophilic amino acid residues are Glu, Lys, Gln and Asp.

Peptides having a beta-sheet conformation are typically characterized by alternating hydrophobic (B) and hydrophilic (L) amino acid residues in adjacent strands as shown below.

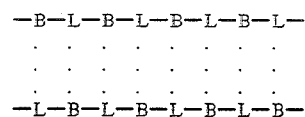

The adjacent strands of amino acid residue sequences in the beta-sheet can proceed in the same (parallel) or different (anti-parallel) directions. The adjacent strands are held together by hydrogen bonding ( . . . ) between a hydrophobic residue in one strand and a hydrophilic residue in the adjacent strand.

Preferred naturally occurring hydrophobic amino acid residues in peptides having a beta-sheet conformation are Val, Ile, Leu and Phe. Preferred hydrophilic amino acid residues in such peptides are Arg, His and Tyr.

A beta-turn conformation comprises a sequence of about 4 amino acid residues that define a reversal in the direction of the peptide. Typically, such reversal in direction is accomplished by hydrogen bonding ( . . . ) between a CO moiety in an amino acid at position i and a NH moiety in the amino acid residue at position i+3 as shown below.

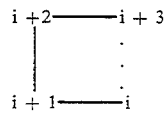

It is to be understood that the direction of the turn can be opposite to that shown above.

Preferred amino acid residues comprising a beta-turn are well known. Chou and Fasman, *Ann. Rev. Biochem.*, 47:251 (1978) at page 258. Preferred amino residues that can occupy positions i and i+3 are His and Cys. Preferred amino acid residues that can occupy position i+1 include L-isomeric amino acids such as Pro, Ser, and Ala. Preferred amino acid residues that can occupy position i+2 include D-isomeric amino acids or L-isomeric amino acids Gly, Asn and Pro.

Linear amphiphilic peptides for use in a metallopolypeptide of this invention can be prepared by a variety of means known to those skilled in the peptide arts. Any method known to produce a peptide is suitable so long as it results in a peptide having the components described herein.

Linear amphiphilic peptides comprising more than about 50 amino acid residues are preferably obtained in recombinant form using well known techniques of genetic engineering. In accordance with such techniques, typically, a DNA sequence that encodes a desired peptide is introduced into an expression vector, which vector is then used to transform a host cell such that the transformed host cell expresses the peptide. Expression vectors used to transform host cells can also include other DNA sequences that encode, for example, promoters that function to produce messenger RNA corresponding to the DNA inserted into the expression vector, factors that increase the translation of the mRNA, antibiotic resistance markers to allow for selection of cells that contain the expression vector, and factors that allow the autonomous replication of the expression vector within the host cells.

Expression vectors have been designed that work in prokaryotic cells such as the bacterium *Escherichia coli*

(*E. coli*) and in eukaryotic cells such as mammalian and insect tissue culture cells. Exemplary prokaryotic expression vectors include the T7 vectors and the $p_L$ vectors.

T7 Vectors include the pT7 series (e.g., pT7-5, pT7-6, and pT7-7) and the pET series. Studier et al., *Methods Enzymol.*, 185:60 (1990). The choice of which vector to use depends upon several factors including the availability of a particular restriction enzyme site into which the DNA sequence of interest is to be cloned, and the presence or absence of a ribosome binding site on the DNA sequence of interest. Vector pT7-7 contains a strong ribosome binding site between a T7 promoter and a multiple cloning site used to insert the DNA sequence of interest into that expression vector.

Another prokaryotic expression vector, a $p_L$ vector, contains the bacteriophage $p_L$ promoter which is regulated by a temperature-sensitive repressor. Exemplary $p_L$ expression vectors containing this promoter are the pSKF series of vectors (e.g., pSKF101, pSKF102, and pSKF201). A DNA sequence of interest is inserted into an appropriate multiple cloning site in such $p_L$ vectors and then used to transform a suitable prokaryotic host cell (e.g., *E. coli* strain AR58). The transformed strain is then grown at an elevated temperature to induce expression from the $p_L$ promoter. The peptide generated by the expression vector containing the DNA sequence of interest can then be isolated according to standard protocols.

Expression of peptides in prokaryotic host cells can assume incorrect conformations because post-translational modification of the expressed peptide does not occur in bacterial cells. Thus, eukaryotic host cells and eukaryotic expression vectors are preferred.

Eukaryotic expression vectors typically contain a mammalian virus origin of replication that allows the expression vector to multiply within the host cell, an efficient promoter element, sequences necessary for messenger RNA processing and polyadenylation, a multiple cloning site to allow introduction of the DNA sequence of interest into the vector, and prokaryotic vector sequences allowing the propagation of these vectors in a bacterial host cell. Promoters in eukaryotic expression vectors are often inducible by, for example, heat shock, heavy metal ions and steroids such as glucocorticoids.

Further, eukaryotic expression vectors often contain selectable markers that allow for the stable integration of the expression vector sequences into the host cell chromosome. Exemplary selectable markers include the aminoglycoside phosphotransferase gene which codes for resistance to the antibiotic G418 (Southern, et al., *J. Mol. Apl. Gen.*, 1:327 (1982), the dihydrofolate reductase gene which codes for methotrexate resistance (Simonsen et al., *Proc. Natl. Acad. Sci.*, 80:2495 (1983), and the thymidine kinase gene, which codes for resistance to aminopterin (HAT medium; Littlefield. *Science*, 145:709 (1964).

The use of these expression vectors in the transfection of mammalian host cells, as well as the recovery of peptides expressed by these vectors, can both be accomplished using standard protocols.

Another useful eukaryotic expression vector system is based upon the baculovirus genome. Baculovirus is a large, enveloped, double stranded DNA virus that infects arthropods (insects). The baculovirus expression system has several advantages over a prokaryotic expression vector system. For example, because the host cells infected with such a vector are eukaryotic (e.g., insect tissue culture cells), post-translational modification can occur. Additionally, the expressed peptides often remain soluble when using this system as opposed to peptide production in prokaryotic cells, which often generate insoluble peptides. Finally, the baculovirus genome is approximately 130 kilobase pairs and, therefore, can accommodate large segments of foreign DNA. Doerfler, et al., 1986, *The Molecular Biology of Baculovirus Virus*, Springer-Verlag, New York. A complete protocol for the use of baculoviruses in the expression of foreign DNA can be found in *Current Protocols in Molecular Biology* (Ausubel et al., eds., John Wiley and Sons, New York, 1989).

Several eukaryotic expression vectors such as the pVL series of vectors (e.g., pVL941, pVL1392, and pVL1393; InVitrogen) are available for use in baculovirus. A DNA sequence encoding a desired peptide is inserted into a multiple cloning site of these expression vectors, and then cotransfected into insect tissue culture cells along with intact baculovirus DNA to provide viral functions which allow the expression of peptides from the baculoviral expression vector. Large quantities of recombinant virus can be produced in insect tissue culture cells to permit the accumulation of the peptide of interest.

DNA sequences of fewer than about 150 base pairs can be synthesized using standard solid-phase procedures as is well known in the art. See, e.g., Oligonucleotide Synthesis: A Practical Approach, ed. by M. J. Gait, IRL Press, Oxford (1984).

DNA sequences of more than about 150 base pairs can be synthesized using the well known mutually priming long oligonucleotide method. *Current Protocols in Molecular Biology* (Ausubel et al., eds., John Wiley and Sons, New York, 1989).

Briefly, the method involves the generation of two pairs (I and II) of long oligonucleotides of approximately 100 base pairs in length. The 3' ends of both pair I oligonucleotides are complementary (the 3' ends have cohesive ends such that they can anneal and form a stretch of duplex DNA). The 3' ends of both pair II oligonucleotides are also complementary but are of a different sequence than the 3' ends of the pair I oligonucleotides. The 5' end of the first oligonucleotide of pair I defines a given restriction enzyme recognition site, designated A. The 5' end of the first oligonucleotides of pair II defines a second restriction enzyme recognition site, designated C. The 5' ends of the second oligonucleotides of both pair I and II both define a third restriction enzyme recognition site, designated B. Oligonucleotide pairs I and II are both placed in solution and allowed to anneal by their 3' complementary, cohesive ends. The short duplex DNA region of each pair created by this 3' annealing allows a modified T7 DNA polymerase to use the first and second oligonucleotides of each pair as both template and primer to complete the synthesis of a duplex molecule comprising the entire length of the annealed oligonucleotides (about 200 bases). This is known as mutually primed synthesis.

This mutually primed synthesis generates two DNA duplex molecules (one for each of pair I and pair II), one of which (pair I) has at one end restriction enzyme site A and at the other end restriction site B, the other of which duplex (pair II) has restriction site B at one end and restriction site C at the other end. These DNA duplex molecules are then digested with restriction enzyme B and ligated to each other to form a single DNA sequence of about 400 base pairs.

By synthesizing several such 400 base pair DNA segments, a DNA segment of any size with a known sequence can be produced.

A subject peptide can also be prepared using the solid-phase synthetic chemistry technique initially described by Merrifield, in *J. Am. Chem. Soc.*, 85:2149 (1963). Synthetic chemistry techniques are preferred for smaller peptides, i.e., having less than about 50 residues, for reasons of purity, freedom from undesired side products, ease of production and the like. Other peptide synthesis techniques may be found, for example, in M. Bodansky, et al., *Peptide Synthesis*, John Wiley & Sons, 2d Ed. (1976) as well as in other reference works known to those skilled in the art. A summary of peptide synthesis techniques may be found in J. Stuart and J. D. Young, *Solid Phase Peptide Synthesis*, Pierce Chemical Company, Rockford, Ill., 3d Ed., Neurath, H. et al., Eds., p. 104–237, Academic Press, New York, N.Y. (1976). Appropriate protective groups for use in such synthesis can be found in the above texts as well as in J. F. W. McOmie, *Protective Groups in Organic Chemistry*, Plenum Press, New York, NE (1973).

In general, those synthetic methods comprise the sequential addition of one or more amino acid residues or suitably protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group such as lysine.

Using a solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted under conditions suitable for forming the amid linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence any remaining terminal and side group protecting groups (and solid support) are removed sequentially or concurrently (if desired), to provide the final peptide.

Where a peptide contains non-naturally occurring amino acid residues, present technologies may not permit the use of recombinant nucleic acid methodologies for the peptide preparation. Presently, protein expression from cloned genes is limited by the ability of a transfer ribonucleic acid molecule (tRNA) to carry amino acid residues into the enzyme complex responsible for protein synthesis. For these non-naturally occurring amino acids that are not recognized by a tRNA or by the enzymes involved in protein synthesis by a recombinant nucleic acid method, peptide synthesis is limited to synthetic means.

(i) Metallopeptide

A non-naturally occurring linear amphiphilic peptide used in this invention can be a metallopeptide. See, e.g., Ghadiri et al., *J. Am. Chem. Soc.*, 112:1630 (1990) and Ghadiri et al., *J. Am. Chem. Soc.*, 112:9633 (1990). A metallopeptide useful in this invention comprises a peptide having an amino acid residue sequence that includes a sequence of amino acid residues that form an alpha-helix, a beta-turn or a beta-sheet rather than a random coil structure in solutions.

A metallopeptide is further characterized as a peptide complexed with (bound to) a metal cation through ligands provided by a pair of coordinating amino acid residues in the peptide. The pair of coordinating amino acid residues provides ligand contacts to the metal ion in a geometry that coordinates the complexation of the metal cation. Thus, the pair of coordinating amino acid residues form a metal binding site on the peptide by providing metal-ligand coordinating contacts for complexing the metal cation. Furthermore, the peptide is bonded to the metal cation such that the metallopeptide has a secondary structure that is stabilized by the bonded metal cation.

The structure and stereochemistry of metallopeptide interactions is generally well understood. See, for example, Freeman et al., *Adv. Protein Chem.*, 22:257 (1967); Kannan et al., *Annals. N.Y. Acad. Sci.*, 429:49 (1984); and Tainer et al., *J. Mol. Biol.*, 160:181 (1982). Additional metallopeptide structures are described in three dimensions by the crystal structure information in the Brookhaven Data Bank, and by the glossary of metalloproteins and individual references to each of the metalloproteins found in Appendix 1 of "Prediction of Protein Structure and the principles of Protein Conformation", ed. Fasman, at page 91–94, Plenum Press, N.Y. (1989).

Each of the pair of coordinating amino acid residues provides at least one metal-ligand coordinated contact. Thus, a metal binding site in a metallopeptide of this invention is formed by two, but not three, coordinating amino acid residues.

In one embodiment, the coordinating amino acid residue itself is of a type that provides more than one metal-ligand coordinated contact, i.e., is itself bidentate, tridentate, quadentate, and the like, as discussed herein. Thus, a coordinating amino acid residue provides at least one, but not more than four metal ligand coordinated contacts.

A metal binding site is engineered into a peptide for the purpose of stabilizing a secondary structure of the peptide by the formation of a metallopeptide complex. The complex is present in a composition that typically includes aqueous solvent, and the metal binding site is positioned on the peptide so as to be on an aqueous solvent accessible surface, e.g., on a hydrophilic surface region of the peptide's secondary structure. Thus, a metal binding site and the pair of coordinating amino acid residues are located in a hydrophilic surface region (a solvent exposed hydrophilic surface) of the peptide's secondary structure in order to allow access of the metal binding site to dissolved metal cations in solution.

In one embodiment, therefore, the present invention contemplates the use of a metallopeptide having a stabilized secondary structure comprising a peptide having an amino acid residue sequence, a portion of which sequence forms a secondary structure that includes a hydrophilic region, and a pair of coordinating amino acid residues that defines a metal binding site located in the hydrophilic region, i.e., the coordinating amino acid residues are solvent accessible. A metallopeptide further comprises a metal cation complexed through metal-ligand coordinating contacts to the metal binding site such that each coordinating amino acid residue provides at least one metal-ligand coordinating contact.

In preferred embodiments, the metallopeptide comprises an amino acid residue sequence that forms an alpha-helix, beta-sheet or beta-turn secondary structure with a hydrophilic surface when present in an aqueous solution.

Where the secondary structure is an alpha-helix, the preferred positions of the two coordinating amino acid residue are at the relative positions of i and i+4 on the peptide such that the side groups of the residues extend away from the helix and hydrophilic surface and into the adjacent aqueous solvent of the composition. Stated differently, the coordinating amino acid residues of the metallopeptide are separated by three spacer residues according to the formula:

-Z-U-U-U-B-, where Z and B represent the same or different coordinating amino acid residues and U represents the same or different spacer amino acid residue, preferably a naturally occurring residue.

Where the secondary structure is a beta-sheet having a beta-turn, the preferred positions of the two coordinating amino acid residues are at the relative positions of i and i+3 or at the relative positions of i−1 and i+5 on the peptide such that the side groups of the residues extend away from the plane defined by the beta-strand and beta-turn and extend into the adjacent aqueous solvent of the peptide. Thus the coordinating amino acid residues of the metallopeptide are separated by two or five spacer residues according to the formula:

-Z-U-U-B- or

-Z-U-U-U-U-U-B-, respectively, where Z, B, and U are as defined above.

In a beta-turn structure that includes both a beta-sheet and a beta-turn, conventional nomenclature identifies the residue located in a beta-sheet at a position one residue prior to the beginning of the turn as residue i. Thus the position i−1 is located two residue positions prior to the beginning of a beta-turn.

When preparing and using a metallopeptide having stabilized secondary structures, knowledge of the mechanism of stabilization is used to determine the locations of a predetermined metal binding site. Secondary structures such as alpha-helices and beta-sheets that contain beta-strands and beta-turns are kinetically unfavorable until sufficient interaction occurs between residues of the peptide as to overcome the random coil structure. These principles are particularly applicable to smaller peptides where the disordered structure is less likely to fold into the particular conformation so as to produce a stabilizing interaction.

The nucleating event in the formation of an ordered structure is the stabilization and formation of a first turn, which is the least favorable and therefore, rate limiting step. Once the first turn of an alpha-helix is stabilized, the translocation of stabilization down a region of a peptide having potential to form a helix is catalytic. Thus, the localized stabilization of a pair of residues into the first turn of a helix by metal-peptide complex formation promotes stabilization along the length of the helix. This nucleation event, therefore, can lead to the stabilization of a first helix, which in turn can provide support to stabilize more distant secondary structures such as alpha-helices or beta-strands.

Just as the nucleation event stabilizes an alpha-helix, so does such an initial nucleation event stabilize an entire beta-sheet by nucleating at a beta-turn and translocating down any beta-strands beginning at the beta-turn.

Thus, in the context of stabilization by nucleation, a metal binding site can stabilize a larger peptide secondary structure and contribute to stabilization of a peptide's tertiary structure. Where the peptide to be stabilized is a biologically active molecule having a site for molecular interaction that is required for biological function, it is advantageous to position the stabilizing metal binding site away from the peptide's biologically active site. Translocatable stabilization makes it possible to alter known biologically active peptides without disrupting biological function by locating the metal binding site away from the biologically active region.

An amino acid residue that is present in a metallopeptide and which residue provides a coordinating contact with a metal ion-ligand complex is referred to herein as a coordinating amino acid residue. Amino acid residues suitable for use as a coordinating amino acid residue in a metallopeptide include naturally-occurring amino acid residues known in the art to provide a ligand for metal cations in metalloproteins, and include His, Cys, Met and the like residues.

In preferred embodiments, pairs of coordinating amino acid residues can be His and His, His and Cys or His and Met. Particularly preferred is the pair where each coordinating amino acid residue is His.

In addition to naturally occurring amino acids non-naturally occurring amino acids can also be employed, e.g., amino acid analogs. A clear advantage of using non-naturally occurring amino acids is that much more flexibility can thereby be built into the selection of pairs of amino acid residues that serve to connect the peptide backbone to an appropriate metal ion-ligand complex. The non-naturally occurring amino acid residues can also be used in conjunction with naturally occurring amino acid residues appropriately spaced apart along the peptide chain so that the desired alpha-helices or beta-sheets can be advantageously stabilized. The naturally-occurring amino acid residues suitable for use in this latter application are identical to those described above.

The process of selecting suitable non-naturally-occurring amino acids parallels the selection of naturally-occurring amino acid residues. For example, preferred embodiments of both naturally and non-naturally occurring amino acids include nitrogen or sulfur atoms that bind directly to the metal center, e.g., His and Cys.

A further consideration in the selection of suitable non-naturally occurring amino acids for use in a metallopeptide is the "chelate effect". The "chelate effect" is well known in the art of coordination chemistry and explains why ligands having more than one binding center (metal-ligand coordination contact) show a greater propensity for binding a metal ion than ligands having only one binding center. The nature of the bonding between metal ion and ligand is usually characterized as ionic but it may also be of the covalent type. The chelate effect is a thermodynamic phenomenon in which the stability of a metal-ligand complex is enhanced due to a decrease in entropy upon dissociation of solvent molecules from the metal's coordination sphere upon chelation. Thus, ligands bind strongly and preferentially when they can chelate the metal cation.

In identifying a pair of coordinating amino acid residues and metal ion most suited for stabilizing a particular alpha-helix or beta-sheet secondary structure, the primary criterion is that the ligands bind strongly with the selected metal ion under the relevant reaction conditions. Other variables, such as the length of side chains connecting the terminal groups of non-naturally occurring amino acids with the peptide backbone, can be determined after the appropriate ligand has been identified. This is because the length of the side chain depends upon the type of ligand selected.

Generally, the identification of a preferred ligand for linking to a metal ion can be made by either first determining the desired ligand to be bonded to the peptide backbone, then identifying metal ions that link strongly to that ligand, or the desired metal ion can be first identified with preferred ligands identified subsequently. Thus, preferred ligands are identified and then metal ion candidates are screened for their effectiveness in linking to that ligand. Alternatively, ligands can be screened following identification of a preferred metal ion. Such methods of screening are well known to those skilled in the art.

Metallopeptides can have coordinating amino acid residues substituted at appropriate spacings along the peptide backbone. The side chains of those coordinating amino acid residues can have a spacer group that serves to link the peptide backbone to the binding moiety located at the terminal end of the side chain. Suitable spacing groups include methylene chains, phenyl groups, and combinations thereof. Preferred spacing groups include amido groups that serve to connect the terminal binding group to the side chain. Many other spacing groups are apparent to the skilled practitioner.

Factors considered in the identification of suitable spacer groups include the thermal stability of the spacer group and the ability of the spacer group to avoid interfering with forming alpha-helices or beta-sheets in the folded peptide. Another important factor in identifying a suitable spacer group is the facility of linking a separately prepared ligand to an amino acid. Preferably, the amino acid residue contains a side chain as well as a reaction site that readily reacts with the separately prepared ligand. Exemplary of such reaction schemes is the condensation of an acid group on the side chain with a reactive amino group on the ligand, as well as condensation of a side chain amino functionality with a carboxyl group on the ligand.

A preferred non-naturally occurring coordinating amino acid has a diacetato amino (DAA) terminus on its side chain. The DAA group is preferably incorporated into a resin-bound peptide incorporating two ornithines in the amino acid residue sequence corresponding to the location of the coordinating amino acids. Thus, ornithines are preferentially blocked with t-butoxy-carbonyl (t-Boc) in a-fluorenylmethyloxycarbonyl (F-Moc) blocked peptide. The Boc groups are removed with trifluoroacetic acid (TFA) and then reacted with excess benzyl bromo acetate in diisopropylethylamine. The nitrogen atom of the amino acid is then coupled to acetate groups. Finally, the F-Moc group is removed to give a terminal amino group which can be acetylated if desired.

A second approach to coupling ligands to amino acid side chains involves forming an amido linkage. Thus, for example, 6-chloro nicotinic ester and trimethyl tin pyridine are reacted in the presence of dichloro-bis (triphenylphosphino) palladium catalyst. The product is saponified, protonated to give 5-carboxyl-2,2'-bipyridine, and then combined with deprotected ornithine and dicyclohexyl carbodiimide to form the amido linkage.

Yet another method of coupling a binding ligand moiety, e.g., N—N chelating group, to an amino acid, involves making the Boc derivative of benzylaspartate. The product is coupled to 5-amino-2,2'-bipyridine in dimethylformamide (DMF) in the presence of carbodiimide. The amide carbonyl group is reduced with hydrogen over Pd on charcoal in ethanol. The resulting bidentate amino acid is incorporated into the peptide using standard t-Boc chemistry.

Similar chemistry to that discussed above is used to prepare the ligands illustrated in Table 1.

As described above, the preferred ligand depends upon the selected metal, or vice versa, the selected metal ion depends upon the preferred binding ligand. For example, when a preferred ligand contains a nitrogen lone pair [as when Ru(II) or Ru(III) are used as the stabilizing metal ion], any N-containing compound having a Lewis basicity attributable to the nitrogen lone pair can be used, e.g. pyridine linked to an amino acid. Similarly, whenever the nitrogen center is relatively negatively charged, e.g., with N-pyrrole and porphyrin-like compounds, strong binding pairs can be expected with the metal ion. Additionally, the chelate effect associated with a given binding ligand assists in identifying still further preferred binding ligands. Preferably, two or three coordination sites on the metal are occupied by such a chelating group.

Exemplary preferred nitrogen chelating ligands are include phenanthroline and bipyridine ligands. Such ligands occupy two coordination sites on a preferred metal ion. The phenanthroline and bipyridine ligands can be linked to the peptide backbone conveniently by condensation between the respective N-ligand and a suitable functional group extending from an amino acid backbone unit. For example, aspartic acid or glutacic acid can be linked via the side chain carboxyl group to phenanthroline or bipyridine moieties upon condensation of the amino acid with an amino derivative of the corresponding N-ligand as described previously. Analogously, whenever the preferred ligand contains 1–3 sulfur (neutral or anionic) atoms, the ligand can be linked via an alkylidene side chain and condensation linkage, and the like. Also combinations of nitrogen-containing ligands and sulfur-containing ligands can be employed to coordinate the metal ion.

Other examples of nitrogen derivatives that can serve as preferred ligands include such monodentate ligands as pyridine and pyrazine linked via a spacing group to the backbone chain of the peptide. Other preferred chelating ligands include 1,2-diaminoethane, bispyridylmethane, porphyrin-like chelating ligands that upon deprotonation bind strongly to the metal ion in bidentate fashion, tridentate ligands such as diacetatato amine and tetradentate ligands such as triethylene tetramine. Other mono-, bi- , tri- and tetra-(quad) dentate ligands are presented in Table 1 and still others will be apparent to the skilled practitioner.

Preferred coordinating amino acid residues have the formula:

$$HO_2C-CH(R)-NH_2,$$

where $R=(CH_2)_n-N(CH_2CO_2H)_2$ and n=1, 2, 3 or 4. Particularly preferred is the non-naturally occurring amino acid residue where n=3. A peptide including this preferred coordinating amino acid residue is shown below in Table 2 and is designated peptide SEQ ID NO:11.

Additional preferred embodiments include a coordinating amino acid having the formula:

$$HO_2C-CH(R)-NH_2,$$

where $R=(CH_2)_n-NH-C(O)-5-[2,2'-bipyridyl]$, and n=1, 2 or 3. Particularly preferred is the non-naturally occurring amino acid residue where n=3.

Other preferred embodiments include a coordinating amino acid having the formula:

$$HO_2C-CH(R)-NH_2,$$

where $R=(CH_2)_n-NH-C(O)-5-[1,10-phenanthroline]$ and n=1, 2 or 3.

TABLE 2

Synthetic Peptides

| Peptide Designation (SEQ ID No.) | Amino Acid Residue Sequence |
|---|---|
| 2 | Ac—Ala—Glu—Ala—Ala—Ala—Lys—Glu—Ala—Ala—Ala—Lys—Cys—Ala—Ala—Ala—His—Ala—CONH$_2$ |
| 3 | Ac—Ala—Glu—Ala—Ala—Ala—Lys—Glu—Ala—Ala—Ala—Lys—His—Ala—Ala—Ala—His—Ala—CONH$_2$ |
| 4 | Ac—Ala—Glu—Ala—Ala—Ala—Lys—His—Ala—Ala—Ala—His—Glu—Ala—Ala—Ala—Lys—Ala—CONH$_2$ |
| 5 | Ac—Ala—His—Ala—Ala—Ala—His—Glu—Ala—Ala—Ala—Lys—Glu—Ala—Ala—Ala—Lys—Ala—CONH$_2$ |
| 6 | Ac—Ala—Cys—Ala—Ala—Ala—His—Glu—Ala—Ala—Ala—Lys—Glu—Ala—Ala—Ala—Lys—Ala—CONH$_2$ |
| 7 | Ac—Ala—Ala—His—Ala—Leu—Glu—His—Gln—Ala—Lys—Ala—Leu—Lys—Glu—Ala—Ala—Gln—Lys—Ala—CONH$_2$ |
| 8 | Ac—Ala—Ala—Cys—Ala—Leu—Glu—His—Gln—Ala—Lys—Ala—Leu—Lys—Glu—Ala—Ala—Gln—Lys—Ala—CONH$_2$ |
| 9 | Ac—Ala—Ala—His—Ala—Leu—Glu—Cys—Gln—Ala—Lys—Ala—Leu—Lys—Glu—Ala—Ala—Gln—Lys—Ala—CONH$_2$ |
| 10 | Ac—Ala—Ala—Xaa$_1$—Ala—Leu—Glu—Xaa$_1$—Gln—Ala—Lys—Ala—Leu—Lys—Glu—Ala—Ala—Gln—Lys—Ala—CONH$_2$ |
| 11 | Ac—Ala—Ala—Xaa$_2$—Ala—Leu—Glu—Xaa$_2$—Gln—Ala—Lys—Ala—Leu—Lys—Glu—Ala—Ala—Gln—Lys—Ala—CONH$_2$ |

Ac indicates an acetylated amino terminus.
CONH$_2$ indicates an amidated carboxyl terminus.
Xaa$_1$ at amino acid residue sequence positions 3 and 7 of SEQ ID NO:10 indicates a non-naturally occurring amino acid having the formula:

$$(NH_2)(CO_2H)CH(CH_2)_3NHC(O)(5-[2,2'-bipyridine]).$$

Xaa$_2$ at amino acid residue sequence positions 3 and 7 of SEQ ID NO:11 indicates a non-naturally occurring amino acid having the formula:

$$(NH_2)(CO_2H)CH(CH_2)_3N(CH_2CO_2H)_2.$$

All peptides are referred to herein by sequence identification number e.g., "SEQ ID NO:1" and, are further described in the SEQUENCE LISTING portion of the Specification.

Alternatively, the selected ligands can each incorporate a combination of different types of binding moieties that together coordinately link to the identified metal ion. For example, a diacetatoamino group can be appended to the terminal end of the side chain to generate a non-naturally occurring amino acid that coordinates strongly to the metal center. Similarly, combined amino-sulfide ligands, aminophosphate, amino-sulfonato, amino-carboxylate, and amino-phosphino ligands can be used to chelate the bridging metal ion in a preferred mode to enhance the stability of the peptide configuration.

Once the non-naturally occurring amino acids have been incorporated into the peptide chain, the resulting modified peptide can be reacted with the preferred metal cation by simply admixing the peptide compound in solution with a suitable salt of the identified metal ion. Peptides react with the metal ion via their ligand-attached side chains expelling water molecules from the coordination sphere of the metal ion. The metal ion reacts with two ligands in bridging fashion.

Once the bridging metal ion-containing complexes form, they operate in an "exchange-inert" manner to maintain the integrity of the metal ion-ligand complex, thereby stabilizing the secondary structure of the peptide or protein under the reaction conditions. Preferred ligands are exchange-inert with the metal's coordination sphere, i.e., once the ligand is coordinately to the metal ion it has only a slight tendency to dissociate from the metal ion.

Peptides can also be prepared in which a selected peptide coordinated to a metal ion is prepared for subsequent binding to a target peptide. More typically, the peptide comprises a desired conformation that is to be enhanced. The peptide is bound to a preselected metal ion via two naturally occurring amino acids or one naturally occurring amino acid linked to a non-naturally occurring amino acid at the appropriate separation distance or to non-naturally occurring amino acids linked via the metal ion. Such compositions have enhanced stability in aqueous solution due to the metal-ligand complex structure adopting a favored alpha-helix or beta-sheet conformation in solution.

Metal preferences can be identified for any particular ligand in a particular metallopeptide. See, for example, the results described in Example 3A(2) where metal ion preferences are identified for the metal binding site formed by peptides SEQ ID NO's:2 and 3 of Table 2.

A metal ion that forms an exchange-inert complex in a metallopeptide is preferred. Preferred exchange-inert metal complexes are those involving a tetra-ammonium Ru(III) complex.

Exemplary complexes have the formula:

$$cis[Ru(L)_n(L')(L'')]^{3+},$$

where L' and L" are the coordinating ligands provided by a pair of coordinating amino acid residues; L is a well known mono-, bi-, or tri- dentate ligand such as NH$_3$, ethylenediamine (en), triethylenetatraamine (trien), or 2,2'-bipyridine (bipy); and n is 4 where L is monodentate such as NH$_3$; n is 2 where L is bidentate such as en or bipy; and n is 1 where L is tridentate such as trien.

Ru complexes in the (II) oxidation state are also contemplated as suitable to form exchange-inert metal complexes in a metallopeptide. However, Ru(II) forms exchange-inert metal complexes that are not as inert as Ru(III) complexes.

The metal ion used as a component of a metallopeptide is preferably a polyvalent metal ion as set forth above in relation to metallopolypeptides. The only limitation is that the complexation of such a polyvalent metal ion occurs with the ligands provided by the two coordinating amino acid residues that define the metal binding site of the metallopeptide.

In a particularly preferred embodiment, the metal ion ligand complex is a tetra-amino Ru(III) complex in which the ligands are provided by a pair of His residues at the relative positions of i and i+4. Exemplary is the Ru(III) complex of peptide SEQ ID NO:3 described in Example 2B. In another embodiment, either of the termini can be modified in a metallopeptide composition to further provide stabilization by metal ion-ligand complex formation. By amidating a native carboxyl-terminus of a peptide, the strong charge dipole at the carboxyl-termini is reduced. The reduction in charge facilitates alpha-helix stabilization. A charge reduction at the amino terminus, by acetylating the peptide amino termini, can also facilitate helix stabilization.

The characteristic of further stabilizing alpha-helical secondary structures by removing charge dipoles at the amino and/or carboxyl termini also applies to stabilizing beta-strand and beta-turn structures. Thus, in preferred embodiments, a metallopeptide also comprises a modified amino or carboxyl termini to reduce the charge dipole. Although numerous chemical modifications to the terminal amino acid residues can be used to reduce the charge, preferred modifications are the acetylation of a free amino termini and the amidation of a free carboxyl termini.

Insofar as the energetics of stabilization of secondary structures is dependent on the extent of secondary structure, i.e., the length of the alpha-helix or beta-sheet structure, it is understood that large helical or sheet structures are more energetically favorable than small helical or sheet structures. In this context, the undesirable effect described above of a charged amino or carboxyl termini to destabilize a secondary structure is inversely proportional to the size of the particular secondary structure.

In practice, modification of termini on very large peptides, typically greater than about 30 amino acid residues, does not substantially improve stabilization of secondary structures by metallopeptide complex formation. Thus, the above described modifications of peptide termini are preferably limited to smaller peptides having more unstable secondary structures, namely peptides of fewer than about 30 amino acid residues in length, and preferably of fewer than about 15 amino acid residues in length.

A method for preparing a metallopeptide having stabilized secondary structures typically involves the preparation of a preselected peptide to include coordinating amino acid residues at selected regions of the peptide to provide a metal binding site. An excess of the prepared peptide is then complexed with a metal cation to form a metallopeptide having a metal ion-ligand complex involving contacts between the metal ion ligand complex and each of the pair of coordinating amino acid residues. As described previously, attempts to stabilize secondary structures within peptides have proven difficult due to the unique environment of any given peptide that defines a secondary structure. Thus, the precise bond lengths involved in, for example, an intra chain covalent linkage to stabilize a secondary structure have been successfully determined only in limited case where a peptide secondary structure is well characterized.

A routine procedure is used for determining a preferred metal ion to complex with a metal binding site engineered into a peptide, thereby allowing the preparation of a metallopeptide having a metal-ligand complex and a resulting stabilized secondary structure.

A key feature of such a routine procedure is based on the finite yet varied number of metal ions available for a screening step to determine a preferred metal ion for complexing a preselected and engineered metal binding site and thereby rendering more stable the secondary structure of the peptide that contains the metal binding site.

Of the metal ions available, a range of metal-coordination bond radii, bond angles, and electron sharing propensities are represented such that at least several of the ions will present the appropriate conditions for metal-ligand complexation. Furthermore, some of the complexing metal ions form metal-ligand complexes that measurably, and preferably at least, stabilize a secondary structure present in the resulting metallopeptide. Thus, the advantage and benefit is the reproducible ease with which to identify a structure-stabilizing metal-ligand complex and thereby form a metallopeptide having a stabilized secondary structure.

By substantial stabilization of a peptide's secondary structure is meant that the degree of stabilized secondary structure increases by at least 10% and preferably by at least 50%, when practicing the method for stabilizing a peptide's secondary structure.

Amino acid substitutions included to form a pair of coordinating amino acid residues can be any of the amino acid residues defined above for a metallopeptide. Exemplary are the amino acid residues included in the peptides produced in Example 1, some of which contain pairs of coordinating amino acid residues comprising naturally occurring amino acid residues, and others containing pairs comprising non-naturally occurring amino acid residues.

After a subject peptide has been prepared to contain a pair of coordinating amino acid residues, the peptide is admixed with an aqueous solution containing a metal ion as disclosed above for a metallopeptide in the form of a dissolved metal salt having the metal ion and an acceptable counter ion to form a biological reaction admixture. Acceptable counter ions are preferably monovalent, and have a dissociation constant relative to the ion that is based in favor of dissolution and metallopeptide complex formation.

A biological reaction admixture contains the peptide and the metal ion in a ratio and at concentrations that favor complex formation. Typically, the peptide is present in the admixture at greater than 1 $\mu$M, and preferably greater than 10 $\mu$M. The metal ion is preferably present in at least one molar equivalent of the peptide, and more preferably in excess, such as greater than five molar equivalents to the peptide to assure rapid and complete metal-peptide complex formation when maintained under biological reaction conditions.

The biological reaction admixture is then maintained under biological reaction conditions for a time period sufficient for the metal ion to complex with the peptide in the biological reaction admixture and form a composition containing a metallopeptide. Biological reaction conditions are temperature conditions that maintain solubility of the peptide and the free metal ion solution, and typically is from about 0° C. to about 50° C., preferably from about 4° C. to about 40° C.

Metal ion complexation with ligands in a peptide's metal binding site typically proceeds at a rapid rate, and is essentially complete in the time required to thoroughly mix the solutions to form the biological reaction admixture. However, where the production of the metal ion having the appropriate oxidation state requires a slow reduction step, it is convenient to include in the biological reaction admixture reagents for reducing a metal ion precursor so that, once reduced, the reduced metal ion is available to react with (complex) the peptide. An example of this latter procedure is described in Example 2B, where the ruthenium(III) complex is reduced over six hours by zinc amalgam in the same admixture for complexing the peptide.

Thus, in one embodiment, a method for preparing a metallopeptide having a stabilized secondary structure comprises the steps of:

(a) preparing a peptide having a preselected amino acid residue sequence, a portion of which sequence forms an alpha-helix, beta sheet or beta turn having a hydrophilic region, wherein the peptide includes two coordinating amino acid residues that are aqueous solvent-accessible and that define a metal binding site in said hydrophilic region;

(b) admixing the peptide with a preselected metal ion in aqueous solution, which metal ion forms a metal polypeptide complex at the metal binding site by chemical bonds between the coordinating amino acid residues and metal to form a biological reaction admixture; and (c) maintaining the biological reaction admixture under biological reaction conditions for a time period sufficient for the metal ion to bind to the coordinating amino acid residues through the metal-ligand coordinating contacts and form a metallopeptide having a non-random secondary structure stabilized by the bonded metal ion, i.e., a metallopeptide. The formed metallopeptide is preferably recovered.

In another embodiment of a method to produce a stabilized metallopeptide, it is desirable to determine the preference of an engineered or determined metal binding site for a particular metal ion. By determining the preference, an optimum metal ion peptide complex can be produced that yields a maximum degree of stabilization of the peptide's non-random secondary structure.

The process for determining metal ion preferences by a particular peptide involves first preparing a series of biological reaction admixtures as before, each containing the peptide of interest and also containing a different metal ion. Thereafter, the admixtures are maintained as described before under biological reaction conditions so that the metal ion can complex with the peptide and form a metallopeptide.

Each of the series of maintained biological reaction admixtures is then individually evaluated (determined) for the presence of a stabilized non-random secondary structure, and preferably for the amount (degree) of structure stabilization. The determination is typically conducted by measuring the amount of secondary structure present in a solution of peptide prior to admixture with a metal ion, and then measuring the amount of secondary structure present in the biological reaction admixture after the maintenance step. An increase in detectable non-random secondary structure in the solution when comparing before and after admixture indicates that the metal ion has complexed with the metal binding site of the peptide and thereby stabilized the secondary structure contained therein.

Detecting changes (increases) in secondary structure of a peptide in solution can be conducted by a variety of assays known in the art, and include the optical measurement techniques of circular dichroism (CD), Raman spectrometry, and the physical measurement of susceptibility to heat denaturation. Exemplary methods for measuring circular dichroism and heat denaturation to characterize secondary structures are described in detail in Examples 3A and 3B.

By determining the degree of non-random secondary structure induced in a peptide by the admixture of a particular metal ion, and concurrently evaluating the results using several different metal ions, the preference of a metal binding site for the metal ion is determined. This process of screening several metal ions for their "preference" to bind a particular peptides metal binding site is demonstrated in Example 3A for peptides SEQ ID NO's:2, 3, 5, and 11 of Table 2.

By the results described in Example 3A, it can be seen that for a particular peptide having an engineered metal binding site, one or more metal ions were identified that effectively stabilize the peptide and increase the content of secondary structure in the resulting metallopeptide. Those stabilizing metal ions were readily determined by straight forward screening procedures.

In addition, it is seen that for any particular metal binding site the most preferred metal ion can be different from the preferred ion for a different metal binding site. Note, for example, that peptides SEQ ID NO's:2 and 3 are stabilized preferentially by Cu(II) and Zu(II) [Example 3A(2)], peptides SEQ ID NO'S:3, 4, and 5 are stabilized preferentially by Ni(II) and peptide SEQ ID NO:11 is stabilized preferentially by Cu(II) [Example 3A(3)].

The method for producing a stabilized metallopeptide can, therefore, incorporate the aforementioned screening procedure to determine the preferred metal ion for complexing and stabilizing the non-random secondary structure of a predetermined peptide. In this embodiment, the method comprises in addition to the first three steps (a), (b), and (c) above, the additional steps of:

(d) conducting steps (b) and (c) as before except including a metal ion different from the metal ion admixed in step (b);

(e) determining the relative amount of non-random secondary structure exhibited by the peptide present in each of the maintained biological reaction admixtures formed in steps (c) and (d); and (f) selecting the maintained admixture that exhibits the greatest amount of non-random secondary structure according to the determination of step (e) to form a metallopeptide having a stabilized secondary structure.

In addition to the use of these methods to prepare metallopeptides having an alpha-helical conformation as set forth above, these same methods have been successfully used to prepare metallopeptides having one or more beta-turns as well as a beta-turn with a beta-sheet (See Examples 6A and 6B hereinafter).

When the linear amphiphilic peptide comprises a metallopeptide, the metal ion used to stabilize the metallopeptide is preferably different from the polyvalent metal ion used to link the polypeptide binding ligands of the metallopolypeptide. Further, the metal ion used to stabilize the metallopeptide is selected such that it will not interfere with the formation or stabilization of the polypeptide coordination complex of the metallopolypeptide.

d. Polypeptide Coordinating amino acids—The linear amphiphilic peptides are covalently bonded to the polypeptide binding ligands by a polypeptide coordinating amino acid residue in the linear amphiphilic peptide. The polypeptide coordinating amino acid residue provides polypeptide binding ligand contacts to the polyvalent metal ion in a geometry that coordinates the complexation of the metal ion and stabilizes the topology of the metallopolypeptide.

In one embodiment, the polypeptide coordinating amino acid residue is of a type that provides only one polypeptide binding ligand coordination bond, i.e., is unidentate.

In a metallopolypeptide of this invention, each polypeptide coordinating amino acid residue provides at least one polypeptide binding ligand coordination bond.

The polypeptide coordinating amino acid residue can be located at any site in the linear amphiphilic peptide so long as the covalent bonding of the polypeptide coordinating amino acid residue to the polypeptide binding ligand does not interfere with the conformation of the linear amphiphilic peptide. Preferably, the polypeptide coordinating amino acid residue is located at either the N- or C-terminus of the linear amphiphilic peptide.

The polypeptide coordinating amino acid residue can be a naturally occurring amino acid residue or a non-naturally occurring amino acid residue, e.g., an amino acid residue analog. A clear advantage of using a non-naturally occurring amino acid residue is that much more flexibility can thereby be built into the selection of a polypeptide coordinating amino acid residue that serves to connect the linear amphiphilic peptide to an appropriate polypeptide binding ligand.

The polypeptide coordinating amino residue can be directly covalently bonded to the polypeptide binding ligand or indirectly bonded via a spacer group interspersed between the polypeptide coordinating amino acid residue and the polypeptide binding ligand. The length and nature of the spacer group depends, inter alia, upon the particular binding ligand employed, the nature of the polypeptide coordinating amino acid residue and the desired topology of the metallopolypeptide. Exemplary spacer groups are 4-amino butyric acid, and a 5-carboxybutyl group as is present in an N-substituted imidazole.

e. Confirmation of Topology

Identifying secondary structures in peptides is now a well developed art. See, e.g., the disclosures in Prediction of Protein Structure and the Principles of Protein Conformation, G. D. Fasman, Ed., Plenum Press (1989), particularly Appendices 1 through 5 at pages 303–316, which disclosure is hereby incorporated by reference.

Alternatively, the secondary structure of a peptide can be identified by physical analysis of a specimen of the peptide by, for example, x-ray crystallography and like techniques that provide three dimensional structure data.

The characterization of topology (non-random secondary structure) in metallopolypeptides can be accomplished by a variety of optical measurement techniques including circular dichroism (CD) or Raman spectroscopy, and by x-ray crystallographic means. In addition, predictive models of non-random secondary structure, including identification of hydrophilic regions in a secondary structure, can be prepared by the use of computer-based modeling programs when applied to known primary amino acid residue sequences.

For example, the successful formation of a parallel tetra-helical metallopolypeptide is established by a few direct experiments. First, the polypeptide coordination complex serves as an important spectroscopic probe to establish the formation of a tetrameric construct. UV-Vis absorption and IR vibrational bands characteristic of a given polypeptide coordination complex are used to establish such criteria. In addition, formation of tetrameric metallopolypeptides can be established by size exclusion chromatography, sedimentation equilibrium centrifugation, mass spectroscopy and like techniques.

Where the linear amphiphilic peptides are short, secondary structure is stabilized mainly through intermolecular hydrophobic interactions. Thus, the formation of an intermolecular ensemble is likely accompanied by an increase in the secondary structure content. Therefore, because most linear amphiphilic peptides at low concentrations (1–10 $\mu$M) exhibit random solution conformations, the findings of a high helical content in a tetrameric metallopolypeptide indicates that the peptides have undergone a metal ion-assisted intermolecular self-assembly process.

Further, inter-strand hydrophobic interaction in the tetrameric metallopolypeptide leading to helical stabilization is an expected thermodynamic consequence of our design. First, the loss of translational and rotational entropy, which accompanies the peptides is compensated by the formation of the polypeptide coordination complex. The linear amphiphilic peptides are then held close in space which leads to an entropically favored inter-strand hydrophobic interaction and the onset of helical secondary structure.

Because the formation of tetrakis-pyridyl and imidazolyl complexes necessarily draws the N-termini of four peptides close in space, there are only two thermodynamically allowed modes for parallel interstrand helix-helix interactions that can bring about dramatic secondary structure induction. Either the desired tetra-helical topology is formed with the hydrophobic surface of each helix engaged with the neighboring helices, or only three peptides in the tetrakis complex interact to form a three-stranded helical coiled-coil structure with the fourth subunit adopting a random orientation in solution. These two possibilities can be easily distinguished by measuring the dependence of non-random secondary structure induction on the metallopolypeptide concentration.

The tetra-helical structure lacking a solvent-exposed hydrophobic surface shows CD spectra independent of the metallopolypeptide concentration, whereas the triple-stranded structure having a fourth unmatched linear amphiphilic peptide available for further intermolecular interaction typically displays concentration dependent CD spectra. Formation of two pairs of two stranded coiled-coil structure in the tetrakis metallopolypeptide complex is unlikely because it is well-known that two stranded helical coiled coil structures are not stable with helices of this length. Therefore, the above studies can unequivocally establish the formation a of parallel tetra-helical topology. High resolution structural determination can also be determined by 2 D NMR spectroscopy or X-ray crystallography. 2 D NMR techniques such as COSY, TOCSY, and NOESY are routinely used to establish secondary structure of a de novo designed metallopolypeptides. A few points are important to consider in determining the topology of a tetra-helical metallopolypeptide by NOE and distance geometry calculations.

The metallopolypeptide is made up of four identical helices which on one hand simplifies secondary structure determination (for a C4 symmetric molecule one set of helix signals is expected) and on the other hand makes it difficult to assign most of the inter-helical NOEs. For such a symmetrical molecule, information about topology can be gained by relying on inter-helical NOE effects between side chains of amino acid residues which in the absence of the desired topology likely do not exhibit any NOE effects. The inter-helical NOEs can then be used in distance geometry calculations to give a more refined model of the tetra-helical metallopolypeptide.

II. A Metal-ion Assisted Self-Assembly Synthetic Method

In another aspect, the present invention relates to a metal ion-assisted self-assembly synthetic method of preparing a metallopolypeptide. The synthetic method typically complies with the following design principles:
a) the linear amphiphilic peptides used in the self-assembly method each donate at least one polypeptide binding ligand for coordinate linking to the polyvalent metal ion;
b) the linear amphiphilic peptides are designed in a way that only when the peptides assume their desired non-random conformation (i.e., alpha-helix, beta sheet, beta-turn) are the polypeptide binding ligands close enough in space to link cooperatively with the polyvalent metal ion;
c) the geometry of the polypeptide coordination complex favors the formation of the desired topology and excludes or disfavors other possible structural arrangements; and
d) the polypeptide coordination complex has a sufficiently high formation constant to significantly contribute to the overall thermodynamic stability of the desired metallopolypeptide.

In addition, to significantly simplify the isolation, purification, and physicochemical characterization of the resulting metallopolypeptide ensemble, it is preferred that the metallopolypeptide also exhibit high kinetic stability, i.e., be exchange-inert.

The use of linear amphiphilic peptides in synthesizing metallopolypeptides depends primarily on controlling the number as well as the relative spatial orientation of the linear amphiphilic peptides participating in the assembly process. The binding energy of the polypeptide coordination complex and the stringent geometrical requirements present for a metal ion-polypeptide binding ligand interaction are used to control the oligomeric state as well as the relative orientation of the linear amphiphilic peptides.

Two methods can be employed for the synthesis and construction of a metallopolypeptide having a desired topology. One method (A) comprises the steps of:
a) providing an isolated peptide-ligand conjugate whose peptide portion is a linear amphiphilic peptide and whose ligand portion is a polypeptide binding ligand that forms a polypeptide coordination complex with a water-soluble polyvalent metal ion having 2 to 8 coordination sites;
b) admixing an excess of said peptide-ligand conjugate in a liquid medium with said water-soluble polyvalent metal ion to form a reaction mixture, said excess referring to the moles of said peptide-ligand conjugate over the moles of said polyvalent metal ion coordination sites; and
c) maintaining said reaction mixture for a time period and under conditions sufficient for said peptide-ligand conjugate and said polyvalent metal ion to form a metallopolypeptide having 2 to 8 linear amphiphilic peptides.

A second method (B) comprises the steps of:
a) providing a polypeptide coordination complex in a liquid medium having a water-soluble polyvalent metal ion with 2 to 8 coordination sites linked to 2 to 8 polypeptide binding ligands;
b) admixing said polypeptide coordination complex with an excess of linear amphiphilic peptide to form a reaction mixture, said excess referring to the moles of said linear amphiphilic peptide over the moles of said polypeptide coordination complex; and
c) maintaining said reaction mixture for a time period and, under conditions sufficient for said polypeptide coordination complex and said linear amphiphilic peptide to form a metallopolypeptide having 2 to 8 linear amphiphilic peptides.

According to method (A), a linear amphiphilic peptide having a polypeptide coordinating amino acid residue is synthesized, for example, on a benzhydryl amine resin by standard Merrifield solid-phase methodology.

The resin-bound peptide is then reacted with a spacer moiety and a polypeptide binding ligand to form a peptide-ligand conjugate. For example, where the polypeptide binding ligand is 3-carboxylpyridine and the spacer group is aminobutyric acid, the resin-bound peptide is reacted with t-Boc protected 4-aminobutyric acid, and then after t-Boc deprotection and treatment with TFA, coupled with nicotinic acid (3-carboxylpyridine) by a standard DCC-Hobt method.

Where the polypeptide binding ligand is imidazolyl and the spacer group is 5-carboxybutyl, the resin-bound peptide is reacted directly with 5-(1-imidazolyl)pentanoic acid. 5-(1-imidazolyl) pentanoic acid can be synthesized in one step by reacting excess sodium imidazolate with 5-bromo or 5-chloropentanoic acid in DMF or tetrahydrofuran (THF) as is well known in the art. Similar N-substituted $C_1$-$C_5$ alkylcarboxy imidazoles can be prepared by similar chemistry using a similar omega-halo $C_2$-$C_6$ carboxylic acid such as 2chloroacetic or 6-chlorohexanoic acids.

The resin-bound peptide-ligand conjugate is then treated with anhydrous hydrofluoric acid (HF) under standard conditions to afford side chain deprotected, resin-free peptides (both pyridyl and imidazolyl moieties are highly stable to anhydrous acids). Peptide-ligand conjugates are then typically isolated and purified by reverse phase high pressure liquid chromatography (RP HPLC) and characterized by amino acid analysis and mass spectroscopy.

Polypeptide coordination complexes are formed by admixing the peptide-ligand conjugate in a liquid medium with a water-soluble polyvalent ion having 2 to 8 coordination sites to form a reaction mixture.

The reaction mixture is maintained for a time period and under conditions sufficient to form a metallopolypeptide comprising 2 to 8 linear amphiphilic peptides. The time and conditions needed to form a metallopolypeptide are dependent upon the polyvalent metal ion and peptide-ligand conjugate as is well-known in the art.

The relative proportions of peptide-ligand conjugate and metal ions used to form exchange-labile polypeptide coordination complexes are dependent primarily on the affinity of the polyvalent metal ion for a particular binding ligand. Typically, peptide is present in molar excess of the polyvalent metal ion coordination sites to ensure coordination complex formation.

The relative proportion of peptide-ligand conjugate to polyvalent metal ion coordination sites used to form exchange-inert coordination complexes can range from about 2:1 to 1:1. Preferably, the peptide-ligand conjugate is present in a molar excess to the number of polyvalent metal ion coordination sites.

The formation of exchange-inert polypeptide coordination complexes is primarily dependent on careful choice of a polyvalent metal ion, its oxidation state, and the polypeptide binding ligands employed. For example, when the metallopolypeptide has a tri-helical topology, Ru can be used to form exchange-inert polypeptide coordination complexes with bipyridine binding ligands. Similarly, Rh can be employed to form exchange-inert polypeptide coordination complexes with both pyridyl and imidazolyl binding ligands. The synthesis of exchange-inert coordination complexes between Rh and pyridyl or imidazolyl binding ligands can be facilitated by generating catalytic amounts of Rh having lower oxidation states.

When the metallopolypeptide has a parallel tetra-helical topology, exchange-inert polypeptide coordination complexes can be formed between Ru and pyridyl or imidazolyl binding ligands. Ruthenium blue is a mixture of $RuCl_3H_2O$ in 50% aqueous ethanol prepared by refluxing under an inert atmosphere. An excess amount of a linear amphiphilic peptide covalently bound to a pyridyl binding ligand is then added to the blue solution and the mixture heated to about 65°-70° C. for few hours. The progress of the reaction can be monitored by absorption spectroscopy.

Polypeptide coordination complexes used in this preparation are synthesized and characterized according to published procedures. For example, when the metallopolypeptide has a parallel tetra-helical topology, labile complexes of the type trans-$[M(L)_4Cl_2]$, where L=a pyridyl-ligated peptide, M=Ni(II); and where L=an imidazolyl-ligated peptide, M=Cu(II), Ni(II), and Co (II) can be formed by addition of corresponding metal halide salts to the peptide solutions. Formation of the desired polypeptide coordination complex can be monitored by absorption and CD spectroscopy.

Exchange-inert polypeptide coordination complexes are preferably formed between the polyvalent metal ions Rh, Ru, Pd, or Pt and pyridyl or imidazolyl binding ligands. Where a number of reactive side chain functionalities are present in a linear amphiphilic peptide, chemoselectivity in the formation of an exchange-inert metal complex is primarily dependent on careful choice of a polyvalent metal ion, its oxidation state, and the polypeptide binding ligands employed. Imidazolyl and pyridyl binding ligands are good $\pi$-acid $\pi$-acceptor ligands and are thus preferred. An exchange-inert macrocyclic cis-$[Ru(NH_3)_4(L)_2]^{3+}$ complex where L denotes imidazolyl side chains of two His residues in positions i and i+4 of a peptide is described in Example 2B.

Rhodium(III) complexes of both pyridyl and imidazolyl binding ligands are synthesized with attention to the following experimental facts. Simple substitution of $RhCl_3$ with pyridyl and imidazolyl ligands is difficult due to the inertness of Rh(III) complexes. The synthesis of Rh(III) complexes is facilitated by generating catalytic amounts of lower oxidation states of rhodium. Reducing agents such as phosphinic acid, hydrogen phosphite, acetaldehyde, alcohols, tin(II) $NaBH_4$, $H_2$, and hydrazine have been widely used in the synthesis of Rh(III) complexes. Formation of Rh(I) and a 2-electron bridge activated complex mechanism has been shown to be involved in the catalysis reaction. This type of strategy has great utility in devising synthetic routes among the inert and robust complexes of rhodium, ruthenium and platinum complexes.

Reducing agents such as phosphinic acid, acetaldehyde, alcohols, tin(II), $NaBH_4$, $H_2$, and hydrazine are used to synthesize Rh(III) complexes. Formation of Rh(I) and a 2-electron bridge activated complex mechanism has been shown to be involved in the catalysis reaction. Therefore, addition of excess peptide-ligand conjugates (pyridyl or imidazolyl) to an aqueous solution of $RhCl_3H_2O$ in presence of catalytic amounts of a reducing agent at 50°-80° C. can provide the desired polypeptide coordination complexes after the usual purification steps. The formation of the desired complex can be monitored by UV, Vis, IR, atomic absorption, and mass spectroscopy.

Addition of excess pyridyl or imidazolyl-ligated peptides to an aqueous solution of $RhCl_3.3H_2O$ in the presence of catalytic amounts of a reducing agent at 50°-80° C. furnishes the desired complexes, followed by the usual purification steps. Formation of the desired complex can be monitored by UV, Vis, IR, atomic absorption, and mass spectroscopy.

In a similar manner, a tetrakis-Ru(II)pyridyl-linked peptide complex can be synthesized. "Ruthenium blue" is prepared by refluxing a mixture of $RuCl_3xH_2O$ in 50% aqueous ethanol under an inert atmosphere. An excess amount of the pyridyl-peptide is then added to the blue solution and the mixture is heated to 65°-70° C. for few hours. The progress of the reaction can be monitored by absorption spectroscopy.

According to a second synthetic method (B), a polypeptide coordination complex is prepared and then reacted in a liquid medium with linear amphiphilic peptide to form a metallopolypeptide.

For example, a synthetic method for the formation of exchange inert metallopolypeptides having polypeptide coordination complexes of the type trans-$[Rh(L)_4Cl_2]^+$, trans-$[Ru(L)_4Cl_2]$, $[Pd(L_4)]^{2+}$, and $[Pt(L_4)]^{2+}$ in which L=3-carboxylpyridine or a before-described N-substituted imidazole is carried out, for example, as follows.

The 15-residue peptide of SEQ ID NO:21 with an $N^\alpha$-F-Moc protected Gly residue is chemically synthesized by standard solid-phase peptide synthesis on, for example, a benzhydrylamine resin. After HF cleavage, the peptide is purified on RP HPLC. The three $N^\epsilon$-amino side chain functionalities of Lys, which can interfere with the coupling step are reprotected as the t-Boc carbamates by standard techniques to form an $N^\epsilon$ protected peptide. It is not necessary to protect the side-chain carboxyl groups of Glu residue because the peptide fragment is used as the amine component in the subsequent fragment coupling. This strategy is advantageous by virtue of enhanced water solubility (vs. the fully side chain protected peptide fragments) and ease of subsequent purification steps. After the removal of F-Moc by base treatment, the $N^\epsilon$ protected peptide is purified by RP HPLC and characterized by mass spectroscopy.

Metal complexes used in this preparation are synthesized and characterized according to well known procedures. See, e.g., Madaule-Aubry et al., *Acta Cryst.,* 324:754 (1968); Eilbeck et al., *J. Chem. Soc.,* 757 (1967); Dobinson et al., *J. Chem. Soc. Chem. Commun.,* 62 (1967); Rund et al., *Inorg. Chem.,* 3:658 (1964); and Cingi et al., *J. Inorg. Chimica Acta,* 39:265 (1980).

For example, a complex of the formula $[Rh(L)_4Cl_2]Cl$ is formed by reacting (with heat) a polypeptide binding ligand with $RhCl_3.3H_2O$ in the presence of ethanol and dimethylsulfoxide (DMSO). A palladium complex of the formula $Pd(L_4)Cl_2$ is formed by reacting (with heat) a polypeptide binding ligand with $Pd(CH_3CN)_2Cl_2$ in the presence of ethanol and dimethyl formamide (DMF). A platinum complex of the formula $Pt(L_4)Cl_2$ is formed by reacting (with heat) a polypeptide binding ligand with $cis-Pt(DMSO)_2Cl_2$.

An excess amount of the $N^\epsilon$-protected peptide is coupled with the N-hydroxy succinimidoyl ester of an N-alkylene-carboxyl imidazole or omega-amino butyric acid amide of nicotinic acid. The blocked peptide is then reacted with an exchange-labile complex or a complex of the desired metal ion as set forth above to form a desired complex. The reaction, if necessary, can be performed in the presence of denaturants.

A metallopolypeptide formed by any method described herein is preferably recovered and purified.

For both of the above methods, linear amphiphilic peptides of less than about 50 amino acid residues used in the synthetic method are preferably chemically synthesized using standard solid-phase synthetic procedures. For example, a preferred linear amphiphilic peptide that forms an alpha-helix in solution has the formula, reading from left to right in the direction from the amino to the carboxyl terminal:

-Gly-Leu-Ala-Gln-Lys-Leu-Leu-Glu-Ala-Leu-Gln-
Lys-Ala-Leu-Ala-CONH2           (SEQ ID NO:1).

Where the linear amphiphilic peptide contains sidechain amino functional groups (i.e., Lys) in addition to the amino group at the N-terminus, means of protecting such amino functional groups must be utilized to direct bonding between the peptide and a given polypeptide binding ligand. Typically, the amino group that serves as the coordinating amino acid residue is protected with F-Moc and the remaining amino functional groups are protected with t-Boc. In this manner, the coordinating amino acid residue can be deprotected by base treatment for bonding to the polypeptide binding ligand, which base treatment does not effect the t-Boc protected amino groups. Following completion of the synthesis of the metallopolypeptide, the t-Boc protected peptides can then be deprotected by treatment with acids such as HCl or formic acid.

The synthesis of a tri-helical metallopolypeptide and a parallel tetra-helical metallopolypeptide and are described hereinafter in Examples 4 and 5, respectively.

III. Metallopolypeptides having Enzyme, Ionophore and Charge Transfer Properties A metallopolypeptide of this invention has utility as an enzyme, ionophore and charge transfer protein.

a. Oxidase and Reductase Enzyme Properties

A parallel tetra-helical metallopolypeptide comprising Ru or Rh coordinately linked to a pyridyl binding ligand that is covalently bonded to four linear amphiphilic peptides each having an alpha-helical conformation can be activated under appropriate conditions to afford oxidase and reductase enzyme properties.

Figure 1:
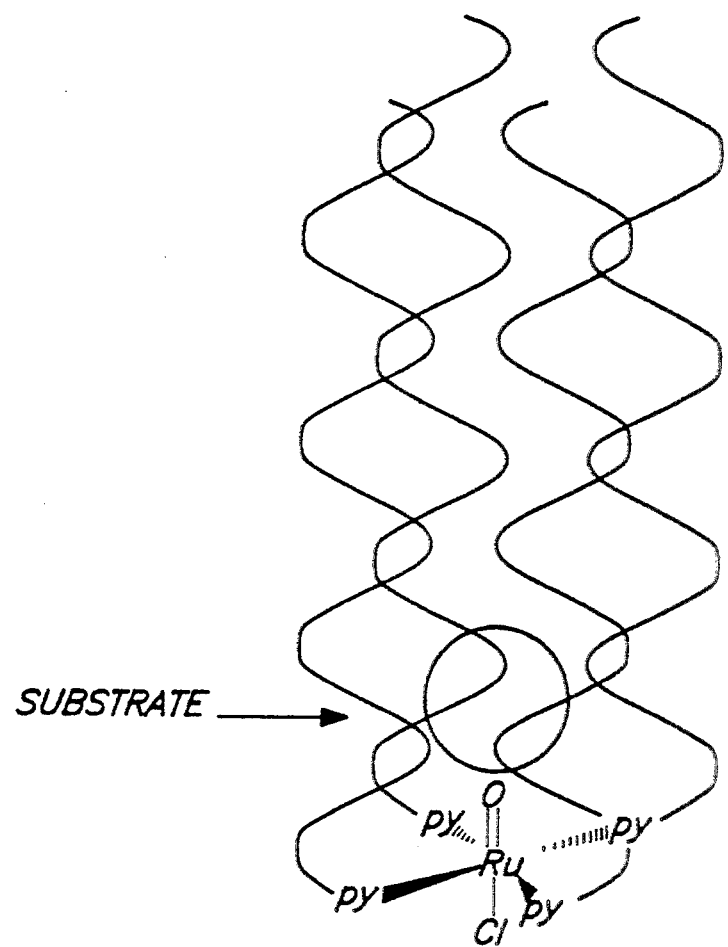
FIG. 1 is a schematic illustration of a parallel tetra-helical metallopolypeptide having a Ru-pyridyl polypeptide coordination complex. The coordination complex forms the bottom of a cavity, which serves to receive a substrate molecule for an oxidation reaction.

The polypeptide coordination complex of a parallel tetra-helical metallopolypeptide is thought to reside at the end of a hydrophobic cavity (FIG. 1). Hydrophobic residues near the termini of the four helical peptides and proximal to the coordinated metal form a hydrophobic dome around the coordination complex.

A Ru-pyridyl coordination complex of the formula $[RuCl_2(py)_4]$ has unique catalytic properties. Under mild conditions this complex can be oxidized to a Ru-(IV)-oxo complex of the formula $trans-[RuCl(O)(py)_4]^+$, which oxo-complex efficiently oxidizes primary alcohols to aldehydes and secondary alcohols as is well known. See, for example Nagao et al. *Inorg. Chem.,* 29:1693 (1990) and the citations therein.

The oxo-complex can function catalytically with high turnovers in the presence of N-methylmorpholine N-oxide (mmo) or tetra-n-butylammoniumperiodate as co-oxidants. Similarly, the tetra-helical bundle metalloprotein can be used as a catalyst for the oxidation of various primary and secondary alcohols.

Rhodium(III) tetrapyridyl coordination complexes are easily reduced to hydrido complexes by the action of hydrogen or NaBH4. Such hydrido-rhodium coordination complexes have been reported to reduce olefins and alkyl halides. Parallel tetra-helical metallopolypeptides comprising the polyvalent metal ion rhodium coordinately linked to pyridyl binding ligands covalently bonded to alpha-helical peptides also have reductase properties.

b. Ionophore Antibiotic properties

An ionophore antibiotic typically exerts its biological function via four interrelated mechanisms. First, the ionophore differentially partitions into the lipid bilayer membrane. Second, at the membrane interface it complexes a metal ion and folds into a lipophilic inclusion complex. Third, the ionophore-metal ion complex, which is now compatible with the apolar membrane interior, then diffuses across the membrane phospholipid bilayer. Finally, at the opposite membrane interface, the complex dissociates, releases the metal ion and diffuses back into the membrane to start the next cycle. The net result of these mechanisms is the transport of a metal ion across the membrane.

Because ionophore catalyzed net metal ion flux across the membrane alters transmembrane electrical potentials and creates metabolic chaos in cells and organs, such ionophores tend to be exceedingly toxic. On the other hand, ionophores which behave as exchange diffusion carriers by exchanging cations across membranes induce minimal net charge translocation across the membrane and consequently have greater potential as therapeutic agents.

The amphiphilic nature of the uncomplexed ionophore confines it to the polar face of the membrane. At the interface it encounters a complexable cation, $M^{2+}$. Once the complex is formed, the molecule encapsulates the ion and forms a neutral lipophilic inclusion complex. The complex, which is now capable of breaking away from the polar interface, passively diffuses across the apolar membrane interior to the opposite membrane interface. Movement of the complex into the polar region of the opposite membrane interface facilitates the release of the cation. The ionophore complexes another cation $N^{2+}$, re-entering the membrane interior, returning to the initial interface and releasing $N^{2+}$. The result is the exchange of one cation for another across the membrane with no net charge translocation. Although most ionophore antibiotics translocate monovalent cations across lipid membranes, there are several potent antibiotics which selectively transport divalent transition metal cations.

Metallopolypeptides are designed to bind a metal ion and fold into a lipophilic inclusion complex. A 14-amino acid residue sequence (see Example 6A) is designed and synthesized to have both a hydrophobic and a hydrophilic character to permit not only sufficient water solubility but also preferential interaction with a lipid interface. Four His and Cys residues are used to bind a metal ion in a tetrahedral geometry. Because of the position of the ligating side chains and the small size of the intervening residues, the peptide backbone is forced to adopt three consecutive turns to bring these side chains into close proximity for metal ion complexation. When the peptide is bound to a metal ion, most hydrophobic side chains are thought to remain exposed on the surface, with the metal ion enclosed in the solvent inaccessible interior of the structure, i.e., it forms a lipophilic inclusion complex.

The topology of the metallopolypeptide ionophore is determined by two-dimensional nuclear magnetic resonance (2 D NMR) techniques. The highly compact nature of the metallopolypeptide provides several NOE cross peaks that can then be used in distance geometry calculations. Preliminary 1-D studies show a very well resolved spectrum which considerably simplifies peak assignments.

Preferably, the uncomplexed peptide interacts with a polar face of a lipid membrane. Such a property protects the peptide from water soluble proteolytic enzymes and enhances its bioavailability. The high amphiphilic character of the peptide favors interaction with the lipid interface. The uncomplexed peptide also does not diffuse freely into the lipid interior of the membrane. The imidazolyl side chain of His residues, which are protonated under physiological conditions, are thought to render the uncomplexed peptide membrane impermeable. Upon complexation with a metal ion, the peptide becomes readily soluble in the lipid interior of the membrane. The selection of particular amino acid residue sequences that have the requisite hydrophobic and hydrophilic properties is based on determination of the partition coefficients of such residues.

Partition coefficients for both complexed and uncomplexed peptides can be readily determined by utilizing dipalmitoyl phosphatidylcholine (DPPC), or dimyristoyl phosphatidylcholine (DMPC) vesicles. Preformed vesicles (150–300 Å in diameter) are first dialyzed (cut off 5000 Å) against an appropriate buffer such as 100 mM sodium borate pH 7.5. The dialysis bag is then placed into a solution with a known peptide concentration in the presence or absence of transition metal ions. The free energy of transfer and the partition coefficient can be determined after an appropriate incubation time by measuring the peptide concentration outside the bag. These studies are performed at various peptide concentrations to make sure that lipid saturation or vesicle disruption are avoided.

The ion transfer properties of metallopolypeptide ionophores is confirmed by measuring the movement of ions across artificial lipid bilayers. Phosphatidylcholine bilayers partitioning or separating two 1–2 ml reservoirs are formed according to well known procedures. A known amount of metal ions $M^{2+}$ and $N^{2+}$ are added separately to each reservoir (ionic strength less than about 0.1M, pH 7.5 buffer). Preferred metal ions for these studies are Zn(II), Cd(II), Cu(II) and Co(II).

A solution of the peptide is then added to one of reservoirs. Aliquots are taken from each reservoir at various time intervals to determine the concentration of $M^{2+}$ and $N^{2+}$ in each reservoir. Metal ion selective indicators are used to colorimetrically determine ion concentrations.

The selectivity of a peptide for a given metal ion is dependent upon the number and type of amino acid residues employed. Theoretical metal ion selectivities for particular polypeptide binding ligand arrangements are provided in Table 3 below.

TABLE 3

Synthetic Polypeptides

| SEQ ID NO. | Peptide | Metal Ion Selectivity |
|---|---|---|
| 12 | Ac—His—Leu—Ser—Val—Val—His—Pro—Gly—His—Thr—Tyr—Ile—Gln—His—$CONH_2$ | $Zn^{2+}$, $Cu^{2+}$, $CO^{2+}$. |
| 13 | Ac—His—Leu—Ser—Val—Val—His—Pro—Gly—His—Thr—Tyr—Ile—Gln—Cys—$CONH_2$ | $Zn^{2+}$, $Co^{2+}$. |
| 14 | Ac—Cys—Leu—Ser—Val—Val—His—Pro—Gly—His—Thr—Tyr—Ile—Gln—Cys—$CONH_2$ | $Zn^{2+}$, $Cd^{2+}$. |
| 15 | Ac—Cys—Leu—Ser—Val—Val—Cys—Pro—Gly—His—Thr—Tyr—Ile—Gln—Cys—$CONH_2$ | $Zn^{2+}$, $Cd^{2+}$. |
| 16 | Ac—Cys—Leu—Ser—Val—Val—Cys—Pro—Gly—Cys—Thr—Tyr—Ile—Gln—Cys—$CONH_2$ | $Cd^{2+}$, $Co^{2+}$. | c. Charge Transfer Properties

Long-range electron transfer has been demonstrated in a wide variety of chemical and biochemical systems. Sequence analyses of membrane proteins indicate that the majority of transmembrane segments are made up of strongly hydrophobic alpha-helical units. In a medium with a low dielectric constant such as the interior of a lipid membrane, hydrogen bonding is favored by about 5–6 Kcalmol$^{-1}$. Therefore, in a membrane environment, formation of alpha-helices is strongly favored because in this conformation a polypeptide can maximize the number of intramolecular hydrogen bonds. A tri-helical metallopolypeptide functionalized at its respective C- and N-termini with tris-bipyridyl metal complexes that spans plasma membranes is designed and synthesized to fix redox active metal ion complexes at opposite sides of a lipid membrane.

For example, the 22-amino acid residue peptide shown below has been designed to have an alpha-helical conformation and to transverse the lipid bilayer.

Gly-Ala-Leu-Ala-Ile-Phe-Leu-Leu-Ile-Ala-Leu-
    Phe-Ala-Leu-Leu-Ala-Ile-Phe-Leu-Leu-Ala-Orn   (SEQ ID NO:17)

The peptide is functionalized at the C- and N-termini with 5-carboxyl substituted 2,2'-bipyridine. An orthagonal solid-phase synthetic approach is used to synthesize this peptide.

The hydrophobic residues forming the core of the peptide were designed to have a sterically favored packing arrangement. The putative exterior of the helical unit, which interacts with the lipid interior of the membrane, preferably comprises bulky hydrophobic amino acid residues.

Vesicles are formed by dispersal of aqueous degassed suspensions of phosphatidylcholine according to well known procedures. Metal ions are added to the solution to entrap those ions inside the vesicles. The vesicles are then purified by gel filtration (Sepadex G-50) against a desired buffer to remove unincorporated and extraneous metal ions and afford uniform size particles. Purified vesicles are ultracentrifuged to yield unilamellar vesicles. The peptide can then be diffused into the vesicle membrane by incubating a solution of the peptide with the vesicle suspension for a few hours.

The peptide was designed with a free carboxyl terminus for the following reasons. Under normal physiological conditions, the carboxyl terminus is deprotonated and bears a negative charge. Because the passage of charged species through the interior of the lipid bilayer is highly disfavored, the free carboxyl terminus should bias which end of the peptide is first inserted into the membrane. In this way, the N-terminal bipyridyl moiety of the peptide likely preferentially forms a tris-chelated complex at the inside surface of the vesicle. The C-terminal complex likely resides at the outside surface.

Incorporation of the peptide into the vesicle can be monitored in several ways. Interaction of the peptide with the interior of the lipid membrane likely leads to enhancement of bipyridyl fluorescence. Because the complexing ions are occluded within the linear aqueous phase of the vesicles, formation of tris-bipyridyl complex at the inner surface of the vesicle can be monitored by UV-Vis spectroscopy to confirm incorporation of the peptide into the vesicles.

In addition, gel filtration studies are used to purify as well as qualitatively establish the binding of the peptide to the vesicles. The vesicles are passed down through a Sephadex G-50 column pre-equilibrated with buffer containing a second metal ion and or reagents. Bound peptide co-elutes with the vesicle fractions (monitored by UV-Vis).

The formation of tris-chelated peptide complexes, hence the trimeric nature the membrane protein, can be verified by absorption spectroscopy. In addition, CD and FT-IR studies are used to establish the helical character of the transmembrane metalloprotein.

An exemplary electron transfer metallopolypeptide comprises the polyvalent metal ions Fe and Co coordinately linked to bipyridine (bpy) binding ligands. The Fe-bpy coordination complex resides on the outside surface of the membrane and is connected through three alpha-helical amphiphilic peptides to a Co-bpy coordination complex at the inner surface of the vesicle. As set forth above, vesicles are formed in the presence of Co(II) ions and a reducing agent such as ascorbate in the inner aqueous phase of the vesicle. Adsorption of the peptide into the vesicles forms a tri-helical metallopolypeptide with the inner coordination complex comprising Co(II). Because of the amphiphilic nature of this coordination complex, it cannot diffuse through the lipid portion of the membrane to the opposite surface and, thus, is confined to the inner surface of the vesicle.

Electron transfer can be turned on by the addition of excess amounts of Fe(III) ions to the vesicle suspension. Upon formation of a polypeptide coordination complex of the formula tris-Fe(bpy)$_3^{3+}$ that is confined to the outside surface of the vesicle, an electron is donated from this complex through the transmembrane triple helical portion of the molecule to the Co(bpy)$_3^{2+}$ acceptor complex. Because ascorbate reduces the potentials for Fe$^{3+}$/Fe$^{2+}$ and Co$^{3+}$/Co$^{2+}$, the net chemical driving force for the electron transfer is about 800 mV or delta G = 18 Kcal·mol$^{-1}$.

The kinetics of electron transfer can be followed by measuring the amount of Fe$^{3+}$ and ascorbate molecules consumed in a given time by standard colorometric, GC, and HPLC techniques.

If charge transfer occurs without any compensating ion migration, substantial transmembrane electrical potentials develop. Further, in the absence of ion diffusion, electrical polarization of the membrane increasingly opposes transmembrane reduction of the externally bound Fe$^{3+}$ ions as the reaction proceeds. To compensate for this effect, potassium selective ion carriers such as valinomycin can be added to the vesicles (buffer solutions used have potassium counter ions). Alternatively, a lipid soluble proton carrier such as carbonyl cyanide m-chlorophenylhydrazone (CCCP) can be added to the vesicles to allow rapid passage of protons.

The following Examples illustrate particular embodiments of the invention and are not limiting of the specification and claims in any way.

EXAMPLES

Example 1

Synthetic Peptides

Synthetic peptides having amino acid residue sequences that correspond to the formulae shown in Table 2 were synthesized by the solid phase method using t-Boc chemistry according to published protocols. Barany, G., *The Peptides*, 2:3 (1979). The synthesized peptides were purified by reverse-phase C$_{18}$ HPLC.

For the synthesis of peptides SEQ ID NO's:10 and 11, having the non-naturally occurring amino acid residues Xaa$_1$ and Xaa$_2$, Xaa$_1$ and Xaa$_2$ were first prepared using conventional synthetic and well known methods, and then were incorporated into the peptide as was done for a naturally occurring amino acid using the solid phase method.

Example 2

Formation of Metallopeptide Complexes

A. Complexing Metal Ions with a Model Alpha-Helix

Peptides SEQ ID NO's:2 and 3 from Table 2 were prepared as set forth in Example 1. The peptides were separately resuspended in either water or a solution of 10 mM sodium borate in the presence of 0.5 mM beta-mercaptoethanol. The resuspended peptides were then admixed with solutions of commercially available salts to form the solutions described in Table 4 having the final concentrations of peptide and metal salt shown.

TABLE 4

| | Peptide Metal Salt Solution Admixtures | | | | | |
|---|---|---|---|---|---|---|
| Study | Peptide | [peptide]$^1$ | Buffer$^2$ | (pH) | Metal | [Metal]$^3$ |
| 1 | 2 | 5.9 | B | 8.0 | No salt | — |
| 2 | 2 | 5.9 | B | 8.0 | CdCl$_2$ | 1.0 |
| 3 | 2 | 5.9 | B | 8.0 | CdCl$_2$ | 2.5 |
| 4 | 2 | 5.9 | B | 8.0 | CdCl$_2$ | 4.0 |
| 5 | 2 | 5.9 | B | 8.0 | CdCl$_2$ | 5.6 |
| 6 | 2 | 5.9 | B | 8.0 | CdCl$_2$ | 15.0 |
| 7 | 2 | 2.2 | W | 6.65 | No salt | — |
| 8 | 2 | 2.2 | W | 6.65 | CdCl$_2$ | 73.0 |
| 9 | 2 | 5.9 | B | 8.0 | ZnCl$_2$ | 5.6 |
| 10 | 3 | 1.8 | B | 6.1 | No salt | — |
| 11 | 3 | 1.8 | B | 6.1 | CuSO$_4$ | 73.0 |
| 12 | 3 | 1.8 | B | 6.1 | CuSO$_4$ | 6.6 |
| 13 | 3 | 1.8 | B | 6.4 | CuSO$_4$ | 7.4 |
| 14 | 3 | 61.0 | B | 7.5 | CdCl$_2$ | 22.0 |
| 15 | 3 | 61.0 | B | 5.3 | CuCl$_2$ | 6.6 |
| 16 | 3 | 61.0 | B | 6.3 | NiCl$_2$ | 21.0 |

TABLE 4-continued

| | | Peptide Metal Salt Solution Admixtures | | | | |
|---|---|---|---|---|---|---|
| Study | Peptide | [peptide][1] | Buffer[2] | (pH) | Metal | [Metal][3] |
| 17 | 3 | 61.0 | B | 7.5 | ZnCl$_2$ | 7.5 |

[1]Peptide concentrations are expressed as ×10$^{-6}$M
[2]B indicates sodium borate; W indicates water.
[3]Metal salt concentrations are expressed as ×10$^{-5}$M.

Nuclear magnetic resonance (NMR) absorption spectra and CD analyses were performed on the above admixtures to evaluate the effects of the admixed metal ions on stability of any alpha-helix present in the admixed peptide. The results of these studies are described below and in Example 3.

Figure 2:
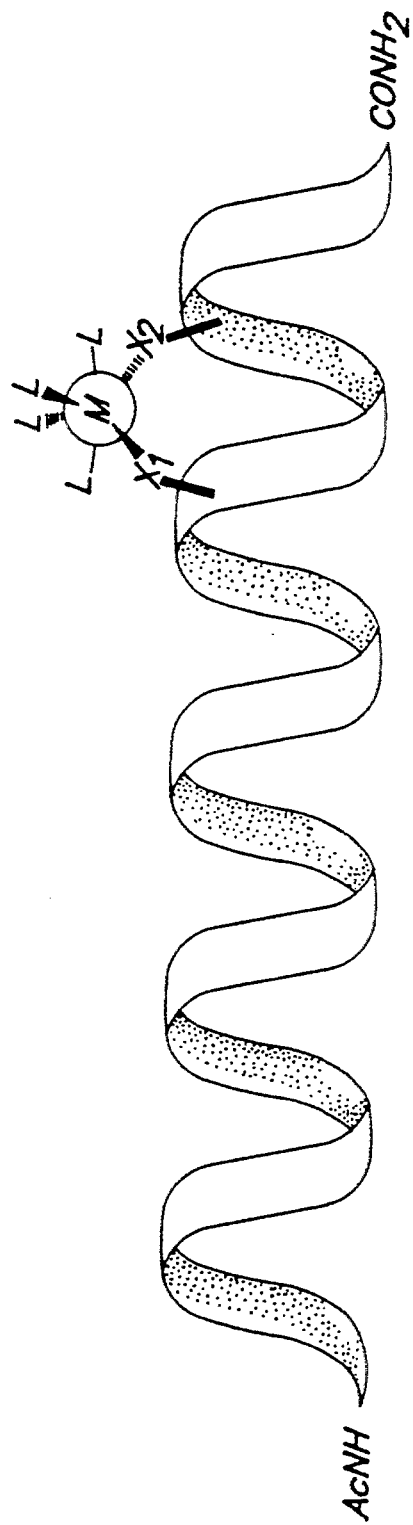
FIG. 2 shows a helix ribbon diagram illustrating metal ion complexation to the side chain of amino acid residues in the i and i+4 positions of an alpha-helix. The N-terminus, designated AcNH, is an acetylated amine. The carboxyl terminus, designated CONH$_2$, is an amidated carboxyl. The metal ion binding site in the amino acid residue sequence is designated by $X_1$ and $X_2$ where peptide SEQ ID NO:2 (Table 2) has cysteine and histidine residues in those locations, respectively, and where peptide SEQ ID NO:3 (Table 2) has two histidine residues at those positions.

A schematic representation of a synthetic peptide in an alpha-helical conformation is shown in FIG. 2. The alpha-helix is stabilized by metal ion complexation to the side chain of the coordinating amino acid residues shown at positions i and i+4. Those positions are labeled $X_1$ and $X_2$, respectively, in the amino acid residue sequence shown in the Figure, whereas the other ligands, L, are ions provided by the metal salt. In peptide SEQ ID NO:2, $X_1$ and $X_2$ are Cys and His residues, respectively. In peptide SEQ ID NO:3, His residues occupy both positions.

B. Forming an Exchange-Inert Metallopeptide Complex Using a Ruthenium Compound

Cis-[Ru(NH$_3$)$_4$Cl$_2$]Cl was prepared according to published procedures. Pellet al., *Inorg. Synthesis*, 26:25 (1989). A solution of cis-[Ru(NH$_3$)$_4$Cl$_2$]Cl was then prepared in degassed 50 mM Tris buffer, pH 7.0, and the ruthenium complex in the solution was reduced in the presence of zinc amalgam to form cis-[Ru(NH$_3$)$_4$(H$_2$O)$_2$]$^{2+}$.

A solution containing peptide SEQ ID NO:3, prepared as in Example 1, in degassed 50 mM Tris buffer, pH 7.1 was admixed with cis-[Ru(NH$_3$)$_4$(H$_2$O)$_2$]$^{2+}$ to form a biological reaction admixture with 10 μM peptide and 50 M ruthenium complex. The biological reaction admixture was maintained at room temperature for 6 hours, and then air oxidized to form a ruthenium peptide SEQ ID NO:3 complex, also referred to generally as a Ru(III)-peptide complex. The complex was then purified and recovered using cation exchange chromatography on a BioRex-70 column (BioRad Laboratories, Richmond, Calif.) to form a composition containing the purified ruthenium-peptide SEQ ID NO:3 complex, i.e., an isolated metallopeptide.

A composition containing a ruthenium-peptide SEQ ID NO:4 complex was similarly prepared by using peptide SEQ ID NO:4, prepared as in Example 1, in place of peptide SEQ ID NO:2 in the above procedures.

The resulting purified ruthenium-peptide complex-containing compositions formed using peptide SEQ ID NO:3 or peptide SEQ ID NO:4 were characterized as being greater than 98% pure when analyzed on analytical reverse phase chromatography using a C18 polysulfoethyl aspartamide RP-HPLC column, or when analyzed on a BioRex-70 cation exchange column. For both compositions, the total ruthenium content was analyzed by atomic absorption spectroscopy and exhibited 1:1 Ru:peptide stoichiometry (±15%). Additionally, both Ru(III)-complexed peptides exhibited the characteristic amino acid analysis patterns and peak heights except for the His peaks which were on average 70% smaller than expected indicating that the His residues were specifically modified. FAB MS of both complexed peptides exhibited the expected molecular weight ion (M/Z=1797) as well as a prominent peak at 1729 corresponding to the loss of four NH$_3$ ligands.

C. NMR Identification of Metallopeptide Complex Formation

The Cd(II) or Zn(II) ion-containing peptide metal salt solution admixtures prepared as in Example 2A were subjected to NMR to identify metallopeptide complex ligands. The results of NMR studies showed that both of histidine 2H and 4H resonances in peptide SEQ ID NO:3 (2.5 mM in D$_2$O, pH 6.6) occurring at δ7.87, 7.74, and δ6.89, 6.87 respectively shifted upfield, upon addition of Zn(II), to δ7.75, 7.71, and δ6.87, 6.67, respectively. Similar results were obtained for peptide SEQ ID NO:2 (2.5 mM in D$_2$O, pH 6.5) in the absence (δ7.91 and 6.95) and the presence of Cd(II) (δ7.71 and 6.91). Of the 17 backbone amide protons in peptide SEQ ID NO:2 (3.0 mM, CdCl$_2$ 0.3M in H$_2$O, pH 5.1), 11 have been sequentially assigned using COSY and NOESY spectra. Amide resonances for N-terminal amino acid residues of peptide SEQ ID NO:2 exhibited $^3$JKNα<5 Hz, which is further evidence that helical structure extends to the N-terminus.

The Ru(III)-peptide SEQ ID NO:4 complex prepared in Example 2B was subjected to NMR spectroscopy to evaluate the chemoselective functionalization of the peptide's His residues by the metal salt. The results of these studies showed that the His C-2 and C-4 protons of peptide SEQ ID NO:4 occurring at δ8.52, 8.51 and 7.20, 7.19 respectively underwent dramatic upfield shifts to δ7.47, 7.15 and 6.98, 6.83, respectively, upon attachment to the tetraamineruthenium(II) moiety. Additionally, the His signals in the Ru(III) peptide SEQ ID NO:4 complex, formed upon oxidation, displayed paramagnetic shifting and appeared as broad peaks at δ0.56 and −0.78.

These studies confirmed that metal salts interacted with His residues on synthetic peptides to form macrocyclic bidentate complexes which are exchange-inert over the time for making NMR measurements.

D. Absorption Spectroscopy to Identify Metallopeptide Complexes

The Ru(III)-peptide SEQ ID NO:3 complex prepared as in Example 2B was subjected to absorption spectroscopy to further confirm the formation of a metallopeptide complex.

The results of the absorption spectroscopic analysis showed that the absorption spectrum of the Ru(III) complex of peptide SEQ ID NO:3 exhibited ligand to metal charge transfer bands at 287 nm and 313 nm below pH 6.5, which bands shifted to 376 nm above pH 8 with an isosbestic point at 331 nm.

Absorption spectra analysis of the Ru(III)-peptide SEQ ID NO:4 complex prepared in Example 2B exhibited similar UV spectra and pH profiles when analyzed by absorption spectroscopy. The pronounced shift in absorption maxima with increasing pH value is consistent with the behavior of the Ru(III) ions containing coordinated imidazoles and is attributed to N-H deprotonation at the "pyrrole nitrogen", Sunberg et al., *J. Am. Chem. Soc.*, 96:381 (1974). The absorption data give a pK$_a$ value of 7.5 for the imidazole NH of the coordinated histidine which is 7 orders of magnitude lower than the pK$_a$ of uncomplexed histidine. The spectral similarity with the simple ruthenium(III)imidazole complexes and the characteristically facile metal-ion promoted imidazole NH ionization provide further support for the formation of the metallopeptide complex.

Example 3

Stabilization of Non-Random Secondary Structure

A. Circular Dichroism (CD) to Measure Degree of Stability (1) CD of Peptides SEQ ID NO's:2 and 3 in Presence of Metal Ions The peptide metal salt solution admixtures prepared as in Example 2A were subjected to CD analyses according to published procedures to measure the degree of stability induced by metal ion complexation with peptides. Greenfield et al., *Biochem.*, 8:4108 (1969) and Johnson, *Ann. Rev. Biophys. Chem.*, 17:145 (1988). All CD data reported herein have an uncertainty of ±2 to 5% for a 100% helix, $[\theta]_{222} = -35,000$, and are based on several CD measurements of both peptides SEQ ID NO's:2 and 3 in the presence and absence of metal ions in various TFE/H20 mixtures at $-10°$ to 20° C. The results of these analyses are shown in FIG. 3.

Panel A of FIG. 3 shows the CD spectrum of peptide SEQ ID NO:2 at 20° C. in the presence of increasing amounts of $CdCl_2$. In this study, solutions 2, 3, 4 and 6 of Table 4 were compared to a solution containing peptide SEQ ID NO:2 in the absence of $CdCl_2$. The curves shown from the top (arrow) to the bottom represent the data collected using increasing concentrations of $CdCl_2$.

Figure 3A:
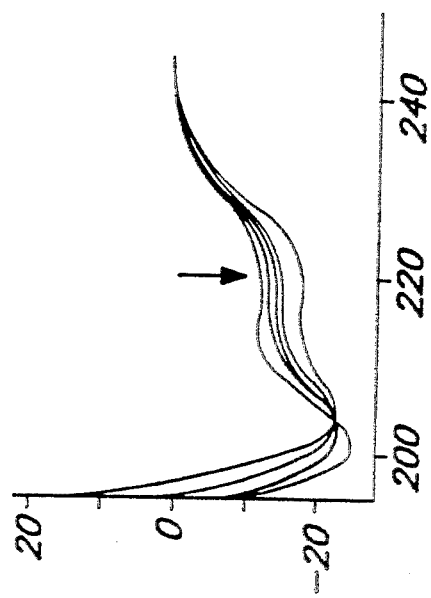
FIG. 3 in three panels as Figures A, B and C illustrates the circular dichroism (CD) spectra of separate solutions of peptides in the presence of metal ion salt solutions measured as described in Example 3A(1). The CD spectra are plotted against increasing wavelength.
Figure 3B:
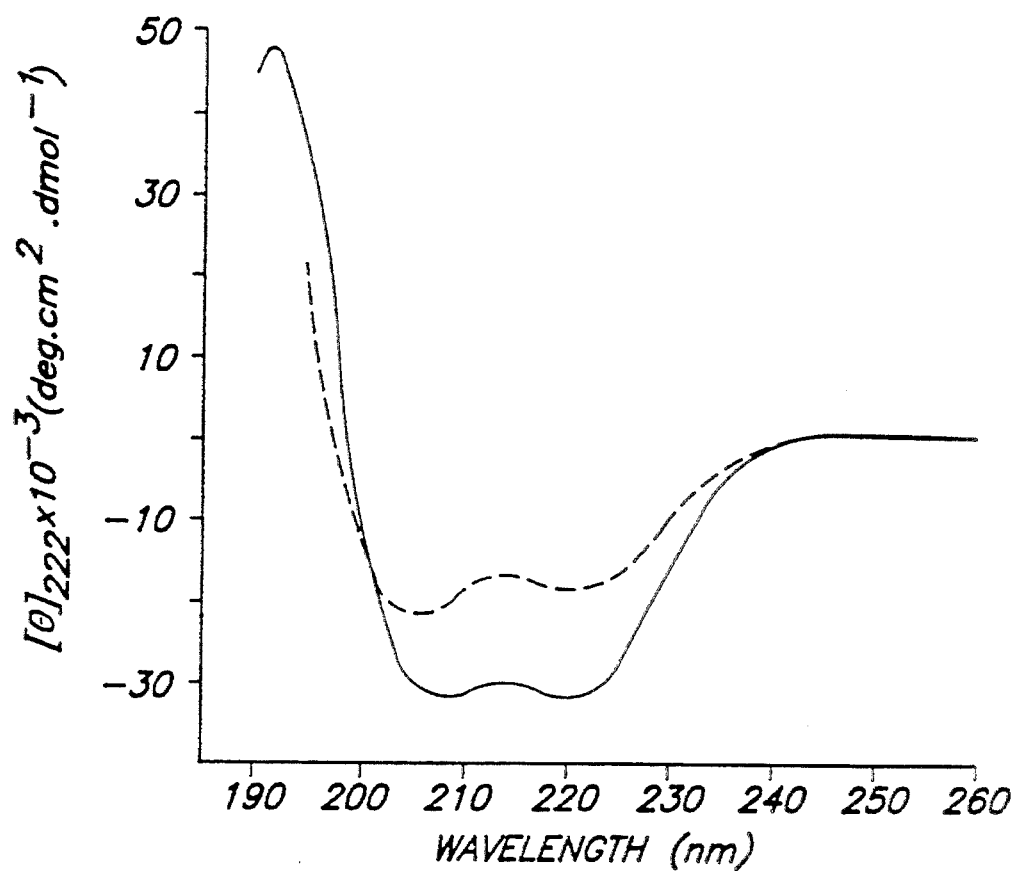

The results of CD analysis of peptide SEQ ID NO:2 admixed with increasing amounts of $CdCl_2$ show an enhancement in the helix content of the peptide by the increase in the 222 nm minima (FIG. 3A). An isodichroic point occurred at 204 nm, which point is characteristic of helix-coil transition. CD spectrum analysis of peptide SEQ ID NO:2 in solution 8 (Table 4) containing $CdCl_2$ was compared to solution 7 without $CdCl_2$ at 4° C. The results of the CD spectrum analysis shown in FIG. 3B (solid curve) indicate that the interaction of cadmium ion with His and Cys side chains at the 16th and 12th amino acid residue positions, respectively (Table 2), provides sufficient stabilization energy to induce up to 90% alpha-helicity ($[\theta]_{222} = -31,500$) at 4° C. In contrast, peptide SEQ ID NO:2 in the absence of metal ion (solution 7) exhibits 54% alpha-helicity ($[\theta]_{222} = 18,800$) at 4° C. (dotted curve).

Figure 3C:
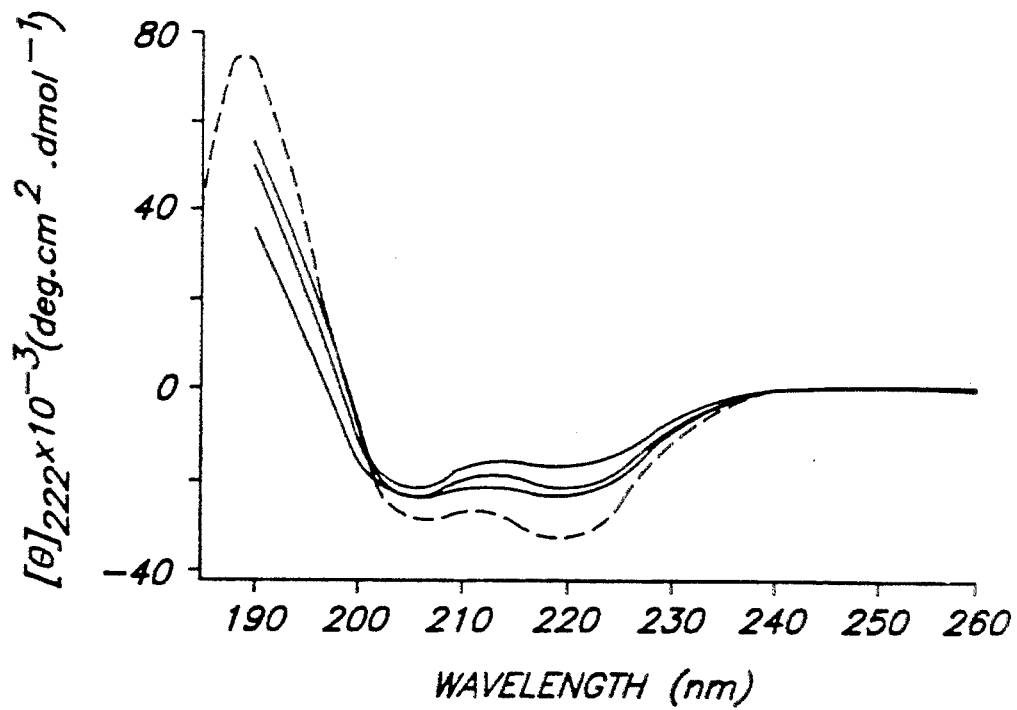

Similar studies were performed with peptide SEQ ID NO:3, which has His residues at both positions 12 and 16 (Table 2), in admixtures with various metal ion salt solutions (Table 4). Solutions of peptide SEQ ID NO:3 in the presence of increasing concentrations of $CuSO_4$ (solutions 11, 12 and 13) were compared with solutions of peptide lacking $CuSO_4$ at 21° C. These results are represented in FIG. 3C by the solid curves as in FIG. 3A. Solution 13 containing peptide SEQ ID NO:3 and $CuSO_4$ was also tested at 0° C. The CD spectral pattern of solution 13 is seen in the dashed curve of FIG. 3C.

The results of the CD spectral analyses show that peptide SEQ ID NO:3 having a pair of His residues at the relative positions of i and i+4 displays about 90% alpha-helicity ($[\theta]_{222} = -31,100$) in the presence of Cu(II) ions at 0° C. The alpha-helical stabilization was slightly enhanced in peptide metal ion solutions maintained at 0° C. compared to those at 21° C. The side chains of His and Cys residues in positions i and i+4 of a peptide, thus, interact with transition metal ions to form a bidentate complex and concurrently fix the peptide backbone in an alpha-helical conformation. In this way, peptides of up to 75% alpha-helicity in water at room temperature and 90% alpha-helicity at 0°–4° C. are obtained.

(2) Metal Ion Selectivity and Affinities of Peptides SEQ ID NO's:2 and 3

Metal ion selectivity is an expected consequence of site specific metal-ligand interaction. The extent of helical induction, to a first approximation, depends on the affinity of metal ion toward the ligands employed, and on the compatibility of metal ion geometry and coordination sphere with the alpha-helical conformation. Thus, although numerous metal ions can induce and stabilize alpha-helix formation, the metal ion having the greatest relative affinity for the ligands employed is preferred and can readily be determined.

To determine the relative affinities of the different metal ions, $CdCl_2$, $CuCl_2$, $NiCl_2$, and $ZnCl_2$, for complexing with the ligands of peptides SEQ ID NO's:2 and 3, the solutions 5, 9, and 14–17 prepared in Example 2B, were subjected to CD analyses as described above. The results of this analysis are shown in FIG. 4. Both Cu(II) and Zn(II) bound peptide SEQ ID NO:3 with similar affinities and increased the helical content to the same extent. On the other hand, Ni(II) exhibited a similar binding constant with respect to Cd(II), but showed higher helical induction. Whereas peptide SEQ ID NO:3 displayed considerable helical induction in the presence of Zn(II), peptide SEQ ID NO:2 was Cd(II) selective and the addition of Zn(II) had no effect on the helical content.

In addition, helicity was independent of concentration of added NaF up to 250 mM for both peptide SEQ ID NO:2 (2.5 µM in 5 mM sodium borate, pH 8.0) and peptide SEQ ID NO:3 (2.0 µM in 5 mM sodium borate, pH 6.1). Peptides Seq. ID No's. 2 and 3 showed CD spectra independent of the peptide concentration in the presence and the absence of metal ions in the measured range of 0.5–70 µM, consistent with intramolecular helical structures. Non-ligated metal coordination sites are most likely occupied by water molecules and addition of external ligands such as 5-nitro-1,10-phenanthroline or mercaptoethanol does not affect the stability of the helical configuration.

(3) Metal Ion Selectivity and Affinities of Other Peptides

Peptides, prepared as in Example 1, and admixed with various metal salt solutions as described in Example 2B, were subjected to CD analysis to characterize metal ion selectivity with respect to the position of the metal binding site in the alpha-helical sequence.

The results of this study indicated that peptide SEQ ID NO:3 binds Ni(II), Cd(II), Cu(II) and Zn(II) in descending order of affinity with Cu(II) and Zn(II) being nearly equivalent. Peptide SEQ ID NO:4 bound Ni(II) and Cu(II) predominantly followed by Cd(II) then Zn(II). Peptide SEQ ID NO:5 bound Ni(II) and Cu(II) in descending order of affinity and exhibited no significant binding of either Cd(II) or Zn(II). Peptide SEQ ID NO:11 bound Cu(II), Hg(II), Cd(II), Fe(II), Zn(II) and Pb(II) in descending order of affinity at a pH of 6.0, with Zn(II) and Pb(II) being equivalent.

The affinity of metal ions for binding sites on alpha-helical peptides is influenced by the sequence position of the amino acids to which they bind. The residues, separated by three amino acid residues, bind Ni(II) with the greatest affinity independent of position in the sequence, N-terminal, middle or C-terminal. Zn(II) is the least effective in binding to the residue in all three positions.

Cu(II) and Cd(II) demonstrated variable affinities dependent on the position of the amino acid residues that contain the binding site. In peptide SEQ ID NO:11, a non-naturally occurring amino acid having a diacetato amino moiety at the side chain terminus was inserted in positions 3 and 7. Cu(II) bound to this moiety with a greater affinity than Hg(II), Cd(II), Fe(II), Zn(II) or Pb(II). The binding of Cu(II) to this non-naturally occurring amino acid residue resulted in the greatest observed stabilization of alpha-helical conformation. At 0° C. using Cu(II), the helicity was about 100% ($\theta = 35,600$), and at 20° C. using Cu(II) the helicity was about 80% ($\theta = 29,300$). The above studies indicated that unprecedented levels of helicity can be induced in short monomeric peptides by taking advantage of selective metal ion complexation.

(4) CD of Ru(III)-Peptide Complexes

Ru(III)-peptide complexes prepared as in Example 2B were subjected to CD analysis to measure the alpha-helical stabilizing effect of ruthenium ions on peptides Seq. ID No's. 3 and 4. The analysis was performed as described above.

The results showed that restriction of the conformational fluxionality of peptides Seq. ID No's. 3 and 4 by the formation of an exchange-inert macrocyclic Ru(III) complex afforded stable alpha-helical metallopeptides. The analysis of CD spectra of Ru(III) complexed peptides Seq. ID No's. 3 and 4 at room temperature in water indicated >80% ($\theta_{222} = -28,000$) and 50% ($\theta_{222} = -17,300$) alpha-helicity, respectively. In contrast, the free peptide SEQ ID NO:3 under similar condition was 45% helical ($\theta_{222} = -16,600$) whereas uncomplexed peptide SEQ ID NO:4 exhibited CD spectrum of a random coil structure. The Ru(III) complexes exhibited CD spectra independent of peptide concentration in the measured range of 0.5 to 300 μM, and were monomeric complexes in solution.

B. Heat Denaturation Assay to Measure Melting Temperatures

In order to assess differences in helix stability between the metal ion complexed and uncomplexed forms of peptides Seq. ID No's. 3 and 4, the conformational stability of each peptide in the presence and absence of transition metal ions was determined from heat denaturation studies according to published procedures. Pace et al., *In Protein structure*, p. 311., IRL Press, (1989). The analysis of the thermal denaturation curves afforded linear $\Delta G$ vs. T and van't Hoff plots. The data indicated that the formation of the exchange-inert Ru(III) complex contributed up to 1 kcal/mol toward the stability of the alpha-helical conformation and dramatically increased the melting temperature of both peptides by about 25° C. Complexed peptides Seq. ID No's. 3 and 4 exhibited melting temperatures (Tm) of 35° C. and 9.5° C., respectively, whereas the corresponding free peptides had Tm values of 11° C. and −15.5° C.

The above studies unequivocally established that exchange-inert metal complexes can be effectively exploited in designing highly stable alpha-helical metallopeptides. The availability of a simple methodology for the formation of stable alpha-helical peptides has considerable utility in the de novo design of biologically active peptides.

Example 4

Synthesis of a Tri-helical Metallopolypeptide

A 15-amino acid residue linear amphiphilic peptide covalently bonded at the N-terminus to a 5-carboxyl-2,2'-bipyridine binding ligand was designed and shown to undergo spontaneous self-assembly, in the presence of a polyvalent metal ion, to form a 45-residue tri-helical metallopolypeptide.

To avoid predisposition toward tri-helical formation, the linear amphiphilic peptide used in this synthetic method was limited to about four helical turns. Although such a short amphiphilic helix can, in principle, participate in various multimeric aggregates, it is not long enough to form stable tri-helical polypeptides in the absence of other stabilizing interactions. Furthermore, although the linear amphiphilic peptide was designed to be compatible with a parallel tri-helical topology, such a peptide does not conform to the heptad repeats implicated in known alpha-helical coiled-coil structures.

The 15-amino acid residue peptide (plus an N-terminal Gly residue) shown below was designed to serve as the linear amphiphilic peptide for metallopolypeptide synthesis.

-Gly-Glu-Leu-Ala-Glu-Gln-Lys-Leu-Glu-Gln-Ala-
  Leu-Gln-Lys-Leu-Ala              (SEQ ID No. 18)

The peptide comprises five amino acid residues that strongly favor helix formation. Hydrophobic and hydrophilic amino acid residues are segregated and each occupy about half of the helix surface (see FIG. 5). Leu and Ala residues comprise the hydrophobic face, whereas Glu, Lys and Gln residues comprise the hydrophilic surface. To maximize favorable charge-helix dipole interactions and to enhance helix stability, the peptide was blocked at the chain ends and Lys and Glu residues were placed near the C- and N-termini, respectively.

Interhelical packing of nonpolar side chains that form the hydrophobic core of the structure was evaluated and the amino acid sequence designed accordingly to afford a sterically favored packing arrangement. Although optimal hydrophobic packing is believed to be essential for the stability of a globular structure, overdesign was avoided on the basis of the static model at hand. The solvent exposed hydrophilic surface was designed to encourage several possible intrahelical as well as interhelical electrostatic interactions. Glycine was used as the coordinating amino acid residue.

To preserve the overall C3 symmetry of the desired tri-helical topology, each linear amphiphilic peptide was designed to donate a bidentate ligand to the putative octahedral coordination complex. A 2,2'-bipyridine derivative was selected as the binding ligand because it provided the most desirable physicochemical properties for the tri-helical topology.

2,2'-Bipyridyl ligands readily react with a variety of polyvalent metal ions to form well characterized trischelated coordination complexes. Further, tris-bipyridyl complexes possess high thermodynamic and kinetic stabilities required for the formation and isolation of the tri-helical topology.

To simplify both design and synthesis, the binding ligand was covalently bonded through the carbon atom at position C-5 to the N-terminus of each Of the linear amphiphilic peptides. Such bonding was shown to minimize steric congestion and ligand-ligand repulsions during the assembly process.

The 15 amino acid residue peptide SEQ ID NO:18 peptide was prepared by employing N-tertbutyloxycarbonyl (Boc) amino acid derivatives for Merrifield solid-phase syntheses. N-α-Boc-L-amino acids were used with the following side chain protecting groups; Glu(OBzl), Lys(Cl-Z). Manual peptide syntheses were carried out in 30-ml vessel fitted with a coarse glass frit. Manual assembly of the protected peptide on a 4-methylbenzhydryl amine resin was carried out at room temperature using the following reaction step cycles. First the Boc protecting group was removed from the α-amino group of the resin-bound amino acid with TFA (50% TFA in $CH_2Cl_2$ for 1 and 20 min). The deprotected peptide resin was then neutralized with 10% DIEA in $CH_2Cl_2$ (2×2 min). Amino acids were coupled to the free α-amino group by the addition of 3 equivalents of Boc-amino acid, 3 equivalent of BOP reagent, and 5.3 equivalent of DIEA in 10 to 15 ml DMF. The reaction was allowed to proceed for the total of 2 hours. The coupling step was monitored by Kaiser test. If second coupling was necessary, the resin was first neutralized with 10% DIEA in dichloromethane.

To prepare 5-carboxyl-2,2'-bipyrdine a solution of 2-chloro-5-ethylnicotinate (2 g. 10.8 mmol), 2-trimethyltinpyridine (2.7 g, 11.3 mmol) and $Pd(Ph_3P)_2Cl_2$ (0.4 g, 0.54 mmol) in dry THF (15 ml) was refluxed for 20 hours. The brown reaction mixture was evaporated, taken up in dichloromethane and filtered through a silica gel-celite bed. Evaporation of solvent gave 5-ethoxycarbonyl-2,2'-bipyrdine as a pale yellow solid (1.3 g, 54%). The crude material was >95% pure as judged by $^1H$ NMR and thin layer chromatography and was used in the next reaction without further purification. $^1H$ NMR ($CDCl_3$, 300 MHz) 6 1.43 (t, J=7 Hz, 3H, $CH_3CH_2$), 4.43(q, J=7 Hz, 2H, $CH_2CH_3$), 7.36 (m, 1H), 7.84(m, 1H), 8.42(m, 1H), 8.50(m,2H), 8.70(d, J−4.2 Hz, 1H), 9.27 (d, J=1.5 Hz). MS (FIV) $(M+H)^+=229$.

The crude ester (1 g, 4.4 mmol) was then taken up in methanol (5 ml) to which was added 1N NaOH (5 ml) and the solution stirred at room temperature for about 3 hours. Solvent was then evaporated and the residue dissolved in a minimum amount of water. The solution was extracted with dichloromethane and the aqueous layer acidified to a pH of 3 with concentrated HCl. The product precipitated as analytically pure white crystals (0.83 g, 95%).

$^1H$ NMR (DMSO, 300 MHz δ7.36 (m, 1H), 7.86 (m, 1H), 8.45(m, 3H), 8.71(d, J=4 Hz, 1H), 9.29(s,1H). MS (FIB) $(M+H)^+=201$

The 5-Carboxyl-2,2'-bipyridine prepared as set forth above was coupled to the N-terminal amino functionality using the DCC-Hobt method. A sample of the resin-bound peptide (1.0 g, 0.23 meq/g) was placed in a 10 ml reaction vessel, and the resin was washed five times with dichloromethane. The terminal Boc protecting group was removed and the resin was neutralized by standard procedures. In a separate flask, 5-carboxyl-2,2'-bipyridine (201 mg, 1.0 mmol), 1-hydroxybenzotriazole monohydrate (153.1 mg, 1.0 mmol), and 4-dimethylaminopyridine (30 mg, 0.25 mmol) were dissolved in 5.0 ml DMF. Diisopropylcarbodiimid (157 μl, 1.0 mmol) was added to this solution and the mixture stirred at room temperature for 30 minutes. The mixture was then transferred to the peptide/resin reaction vessel and was allowed to react for 3–4 hours (until negative kaiser test) with constant shacking. The resin was then washed with DMF (5×) and $CH_2Cl_2$(5×) and dried in vacuo.

The peptide was then deprotected and cleaved from the resin by treatment with HF and purified by reversed-phase $C_{18}$ HPLC. Dried resin was placed in the HF apparatus. Side chain protecting groups as well as the peptide-resin bond were cleaved under "high HF" condition (90% HF, 10% p-cresol) at 0° C. for 2 hours. After removal of HF under vacuum, the peptide-resin residue was placed on a fritted funnel and washed with diethyl ether (5×). The peptide was then dissolved in 10% aqueous acetic acid and filtered through, leaving the resin on the frit. The crude peptide solution was lyophilized and samples of 150–200 mg were redissolved in 2% aqueous acetic acid and were subject to gel filtration on a Sephadex G15 column (2.50 cm) preequilibrated with the same solvent to remove the scavenger and small molecular weight contaminants.

The peptide was then purified by preparative reversed-phase HPLC on a Vydec $C_4$ column using a 20 min linear gradient of 22–63% acetonitrile/water/0.1% TFA with a 9.0 ml/min flow rate. The desired peptide fraction (18 min retention time) was collected, lyophilized, and characterized by amino acid analysis and FIB mass spectroscopy (M/Z=1821). Analytical RP HPLC indicated that the gel-filtered crude peptide was 90% pure and the HPLC purified samples >99% pure.

The purified peptide was then reacted with Ni(II), Co(II), Fe(II) or Ru(II) in an aqueous medium. Aqueous solutions of the peptide in the presence of all tested metal ions displayed absorption spectra characteristic of tris-bipyridyl metal complexes.

Ruthenium trichloride hydrate (0.7 mg, 3.3 μMol) under a argon atmosphere was dissolved in 100 μl of degassed 50% ethanol-water mixture in a 1.0 ml Schlenk-type tube. The reaction mixture was heated at 90° C. for 30 minutes during which time the color of the solution changed from brown to green to dark blue. Bipyridylpeptide (20 mg, 11 μMol) was dissolved in 100 μl of degassed 50% ethanol-water mixture and was added to the ruthenium "blue" solution under an argon atmosphere. The heating was continued for additional 30 minutes. As the reaction progressed, the solution turned from deep blue to a reddish brown color. The reaction mixture was allowed to cool to room temperature and was directly applied to a Sephadex G-25 gel filtration column and elluted with water. The desired metalloprotein complex was then separated from the small amounts of unreacted peptide using ion exchange chromatography on CM-Sephadex C-25 with 0–2M NaCl salt gradient in 50 mM MES pH 6.5 buffer. Final purification as well as desalting was performed using RP HPLC to afford about 15 mg of the desired metalloprotein. Formation of the desired complex was established by FIB mass spectroscopy M/Z=5563 and the following characteristic ultraviolet and visible absorption bands $\lambda_{max}$-(nm) 255; 300; and 470 br.

Proton nuclear magnetic resonance spectra were recorded at 300MHz on Bruker AM300 spectrometer and are reported in parts per million (ppm) downfield from $Me_4Si$. Ultraviolet-visible spectra were recorded on Aviv Associates 14DS and Milton Roy Spectronic 3000 Array spectrometers. Circular dichroism measurements were made on Aviv Associates 62DS spectrometer equipped with a thermostable cell holder using 10, 1, and 0.1 mm Hellma quartz cells. All reported CD data have an uncertainty of ±2–5%. All ellipticity measurements are expressed as mean residue ellipticity, [θ], having the units deg·$cm^2$·$dmol^{-1}$.

Peptide concentrations were determined by quantitative amino acid analysis (average of three runs) using norleucine as internal standard. The FIB positive ion mass spectra were obtained on a VG ZAB-VSE double focusing mass spectrometer equipped with a cesium ion gun. Preparative reversed-phase HPLC was performed on a 2.2×25 cm Vydac $C_4$ (10μ particle size) column using a binary gradient of A: 1% acetonitrile/water/0.1% TFA, B: 90% acetonitrile/water/0.07% TFA. Elution profiles were monitored at 225 and 280 nm. Analytical reversed-phase HPLC was done using a 4.6×250 mm Vydac $C_{18}$ (5μ particle size) column using the above binary gradient.

Guanidine hydrochloride denaturation curves were determined by measuring the mean residue ellipticity at 222 nm on Aviv Associates 62DS spectrometer of solutions containing 450 μM metalloprotein in 100 mM HEPES buffer pH 7.0 as a function of GndHCl concentration in a thermostated 0.1 mm Helma quartz cells. The solutions were kept at 25 C. for at least 1 hour before measurements were made. Each reported data point is the average of sixty consecutive measurements over a period of 1 minute.

Denaturation curves were analyzed using least-squares fit (nonlinear regression program MINSQ) to the following equation;

$$f_u = (exp-(\Delta G(H_2O)/RT - m[D]/RT)/(1 + exp-(\Delta G(H_2O)/RT - m[D]/RT))$$

where $f_u = (\theta_n - \theta_{obs})/(\theta_n \theta_d)$ is the fraction unfolded, [D] is the denaturant concentration, m is the measure of dependence of ΔG on denaturant concentration, $\theta_n$ is the measured $[\theta]_{222}$ for the native conformation, $\theta_d$ is the measured $[\theta]_d$ is the measured $[\theta]_{222}$ for the denatured conformation, and $\theta_{obs}$ is the observed variable parameter.

In the presence of Ni(II), the intra-ligand π-π* absorption bands of the bipyridine moiety occurring at 244 and 290 nm underwent a characteristic bathochromic shift with concomitant splitting of the longer wavelength band into two peaks at 304 and 314 nm. Furthermore, size exclusion chromatography of the peptide under native or denaturing conditions and in the presence and the absence of Co(II) and Ni(II) was also shown to be consistent with the formation of a trimer. Although, the exchange-labile nature of Ni(II) and Co(II) coordination complexes precluded their analysis by FIB MS, [Ru(bipypeptide)]2+ which is an exchange-inert complex, gave a mass spectrum with a peak corresponding to the expected molecular mass ion at M/Z=5563.

The alpha-helical content of the linear amphiphilic peptide increased dramatically in the presence of Ni(II) or Co(II) ions as evidenced by CD spectroscopy. In the absence of any polyvalent metal ion, the peptide (7.4 μM in 5 mM sodium borate, pH 6.4, 21° C.) was only 30% alpha-helical ($\theta_{222} = -10,000$ deg·cm$^2$·dmol$^{-1}$). In the presence of Ni(II) or Co(II) ions under similar conditions, however, the peptide exhibited greater than 70% alpha-helicity ($\theta_{222} = -23,400$ degcm$^2$dmol$^{-1}$). The extent of alpha-helicity was further stabilized (80%, $\theta_{222} = -25,800$ deg·cm$_2$·dmol$^{-1}$) by the presence of 150 mM NaCl.

These data indicated that the peptide underwent a metal ion-assisted intermolecular self-assembly process. Because the formation of a tris-bipyridyl metal complex necessarily draws the N-termini of the three alpha-helical peptides close in space, there are only two possible modes for inter-strand helix—helix interactions that can bring about such dramatic non-random secondary structure induction. Either the desired tri-helical topology is formed with the hydrophobic surface of each helical peptide engaged with the neighboring helices, or only two helical peptides in the tris-bipyridine complex interact to form a two-stranded helical structure with the third helical peptide adopting a random orientation in solution. These two possibilities were distinguished by measuring the dependence of non-random secondary structure induction on the metallopolypeptide concentration.

The tri-helical structure lacking a solvent exposed hydrophobic surface is predicted to show a CD spectra independent of the metallopolypeptide concentration. On the other hand, the double stranded structure having an unmatched helical peptide available for further intermolecular interaction is predicted to display a concentration-dependent CD spectra. As shown in FIG. 6, the alpha-helical content of the metallopolypeptide in the presence of Co(II) remained constant over the peptide concentration range of 5 to 100 μM, thus, indicating that the desired tri-helical topology was formed. Similar behavior was observed in the presence of Fe(II) and Ru(II).

In the absence of added polyvalent metal ions, the peptide underwent the expected concentration dependent intermolecular aggregation to form, surprisingly, a dimeric structure. Such behavior further illustrated the utility of polyvalent metal ions in redirecting or overriding the intrinsic preference of the peptide for the formation of intermolecular structure(s) by selectively stabilizing the tri-helical topology even though such a topology is not the most thermodynamically stable entity in the absence of metal ions.

Because tris-bipyridyl-metal ion coordination complexes are chiral and can form either a left-handed or a right-handed helix, two diastereomeric tri-helical structures can possibly be formed. The stereogenic environment of the ensuing parallel tri-helical topology as well as the geometrical constraints imposed by the overall C3 symmetry of the coordination complex was expected, however, to enforce a high degree of diastereoselectivity in the assembly process. The CD spectrum (in the region of 280 and 330 nm) of the peptide in the presence of Ni(II) indicated the formation of one diastereomer having a left-handed helical configuration. Such a behavior is also consistent with the expected left handed supercoil of the tri-helical metallopolypeptide. The analysis of the thermal denaturation curves for the metallopolypeptide in the presence of Ni(II) yielded linear ΔG vs T and van't Hoff plots. The tri-helical metallopolypeptide exhibited a melting temperature Tm of 41° C. with a free energy of stabilization of 0.6 Kcal/mol.

These data, taken together, show that a polyvalent metal ion-assisted self-assembly process is a simple and effective method for the design and construction of a topologically predetermined metallopolypeptide. The simplicity of this approach permits structure optimization as well as the incorporation of nonproteinogenic amino acids and spectroscopic labels with minimum synthetic effort.

Example 5

Synthesis of a Parallel Tetra-helical Metallopolypeptide

The underlying principle for the design of a peptide sequence that can undergo intermolecular association to form a parallel tetra-helical metallopolypeptide is similar to the one employed in the design of the tri-helical coiled-coil structure of Example 4. According to such a design principle, a polypeptide coordination complexation site must be utilized that is compatible with the overall topology of the target structure.

A parallel tetra-helical metallopolypeptide was made by first synthesizing a non-linear amphiphilic peptide having an alpha-helical conformation by standard solid-phase methods, functionalizing the N-terminus of the peptide with a spacer moiety attached to an imidazoyl polypeptide binding ligand to form a peptide-ligand complex, and then reacting the peptide-ligand complex with a polyvalent metal ion.

In accordance with this synthetic method, the 15-amino acid residue peptide shown below was synthesized by standard Merrifield solid-phase methods on a benzhydryl amine resin.

-Gly-Leu-Ala-Gln-Lys-Leu-Leu-Glu-Ala-Leu-Gln-Lys-Ala-Leu-Ala-CONH$_2$   (SEQ ID No. 1)

The design of the peptide sequence was aided by examining a CPK model of a parallel tetra-helical bundle structure. Interhelical packing of nonpolar side chains which form the hydrophobic core of the structure was evaluated and the amino acid sequence was designed accordingly to afford a sterically favorable packing arrangement. The 14-residue helical portion of the peptide is composed primarily of five amino acid residues which strongly favor helix formation. Polar and nonpolar residues are segregated and each occupy about half of the helix surface. Leu and Ala residues constitute the hydrophobic face while Glu, Lys, and Gln side chain functionalities comprise the hydrophilic surface.

To maximize favorable charge-helix dipole interactions and enhance helix stability, the peptide was blocked at the chain ends, and Lys and Glu residues placed near the C- and N-termini, respectively. The solvent exposed hydrophilic surface was designed to encourage several possible intra- and inter-helical electrostatic interactions.

The peptide was N-capped with a Gly residue followed by a conformationally flexible spacer connecting a polypeptide binding ligand to the peptide.

The length of the spacer was determined by examining CPK models to allow a sterically favored contiguous arrangement of metal ion complexation site and the helical domain.

The N-terminal Gly residue was functionalized by reacting the resin-bound peptide with 5 equivalents of preformed 1-hydroxybenzotriazole ester of nicotinic acid in dimethyl formamide (DMF) in the presence of 10% 4-dimethylaminopyridine (DMAP) for 3 hours to form a pyridyl-peptide complex. The pyridyl-peptide complex was cleaved from the resin by treatment with anhydrous HF, isolated by gel filtration on a Sephadex G-25 column, purified by RP HPLC and characterized by amino acid analysis, $^1$H NMR, FIB-MS and absorption spectroscopy.

Ruthenium trichloride hydrate (0.3 mg, 1.4 μMol) was dissolved in 120 μl of degassed 50% (v/v) ethanol-water in a 1.0 ml Schlenk-type tube to form a reaction mixture and was kept under an argon atmosphere. The reaction mixture was heated at 90° C. for 20 minutes during which time the color of the reaction mixture changed from brown to green to dark blue.

The isolated and purified pyridyl-peptide complex (10 mg, 6.0 μmol), prepared as set forth above, was mixed with the ruthenium blue reaction mixture to form an admixture and the admixture heated at 90° C. for 30 minutes, during which time the admixture changed from dark blue to green. The admixture was applied to a Sephadex G-25 gel filtration column and the peptide-containing fractions collected.

The parallel tetra-helical metallopolypeptide was isolated from unreacted peptide using ion exchange chromatography on CM Sephadex C-25 with a 0–2M NaCl gradient in 50 mM TRIS buffer, pH 7.6. The parallel tetra-helical metallopolypeptide was purified using RP HPLC to yield 7.0 mg.

The parallel tetra-helical metallopolypeptide displayed an absorption spectrum characteristic of a trans [Ru(Py)$_4$Cl$_2$] complex with an absorption band at 256 nm and a broad band centered at 377 nm. In contrast, the pyridyl-peptide complex in the absence of Ru exhibited only a pyridyl absorption band at 260 nm. The formation of the parallel tetra-helical metallopolypeptide was confirmed by a molecular weight determination made using size exclusion chromatography. The CD spectrum of the parallel tetra-helical metallopolypeptide ($\theta_{222} = -29,000$ deg·cm$^2$·dmol$^{-1}$, >90% α-helical) indicated a highly helical structure consistent with such a metallopolypeptide.

Example 6

Metallopeptides having a Beta-Turn Conformation
A. A Metallopeptide having Three Beta-Turns The 14 amino acid residue sequence shown below was designed and synthesized to assume a beta-turn conformation as shown below the primary sequence.

Ac-Cys-Leu-Ser-Val-His-Pro-Gly-His-Thr-Tyr-Ile-Gln-Cys-CONH$_2$   (SEQ ID NO:19)

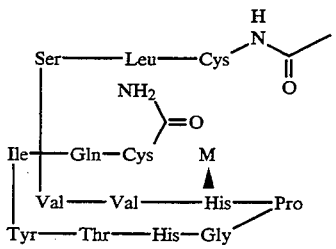

The peptide was prepared using standard Merrifield solid phase procedures and then reacted with Zn(II) in aqueous solution. The metallopeptide comprises three beta-turns with the intervening residues having a beta-sheet conformation. The charge on the Zn metal ion (M) is neutralized by the two Cys residues. The Zn metal ion resides in the interior of the structure with the side chains directed outward toward the solvent.

The peptide, in the absence of a metal ion, was readily soluble (up to about 2 mg/ml, 1.3 mM) in aqueous media at a pH value of from about 4 to about 9. The peptide binds one equivalent of Zn at pH values above about 5.0 with a $K_d = 1$–$5 \times 10^{-6}$M at a pH of about 7.0. The aqueous solubility of the peptide decreases about 100-fold in the presence of Zn at pH values greater than about 5.0.

Data from CD and NMR analyses confirm the beta-turn conformation of the peptide in the presence of Zn. In the absence of added Zn, the peptide (about $6.0 \times 10^{-6}$M in Na borate, pH 7.5) showed a CD spectrum characteristic of a random-coiled structure. The addition of one equivalent of Zn to the peptide caused a dramatic shift in the CD spectrum with a minimum at 230 nm and a maximum at 210 nm to indicate a beta-turn structure. Further, NMR data show that the 2-H and 4-H protons of His underwent chemical shifts in the presence of Zn, which shifts indicated the participation of such His residues in binding Zn.

B. A Metallopeptide having One Beta-Turn

The 12 amino acid residue sequence shown below has been designed and synthesized to assume a beta-turn conformation as shown below the sequence.

Val-Asn-Val-Lys-His-Gly-Ser-His-Asn-Val-Lys-Val-CONH$_2$ (SEQ ID NO:20)

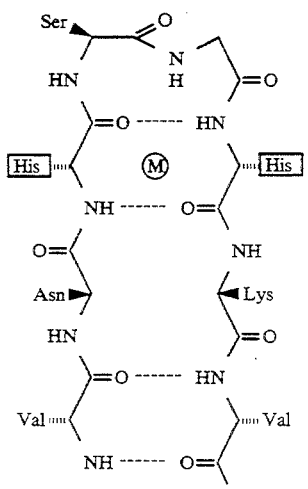

-continued

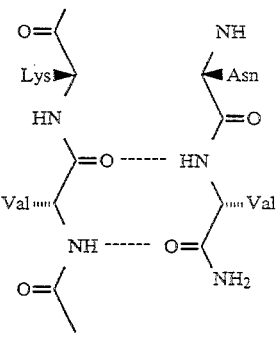

The peptide was prepared using standard Merrifield solid phase procedures and then reacted with Cu(II) in aqueous solution. The metallopeptide comprises one beta-turn with the residues on either side of the turn having a beta-sheet conformation. The topology of the peptide was confirmed by NMR and CD spectral analysis.

The foregoing specification, including the specific embodiments and examples, is intended to be illustrative of the present invention and is not to be taken as limiting. Numerous other variations and modifications can be effected without departing from the true spirit and scope of the present invention.

---

What is claimed:

1. A parallel tetra-helical metallopolypeptide comprising a polyvalent metal ion that is Ru or Rh coordinately linked to 4 polypeptide binding ligands, each of which polypeptide binding ligands is independently covalently bonded to a linear amphiphilic peptide having the formula, reading from left to right in the direction from the N-terminus to the C-terminus:

-Gly-Leu-Ala-Gln-Lys-Leu-Leu-Glu-Ala-Leu-Gln-Lys-ALa-Leu-Ala-CONH$_2$ (SEQ ID NO:1).

2. The metallopolypeptide according to claim 1 wherein the polyvalent metal ion is Ru.

3. The metallopolypeptide according to claim 1 wherein the polypeptide binding ligand is 3-carboxyl-pyridine.

4. A tri-helical metallopolypeptide comprising a polyvalent metal ion selected from the group consisting of Co, Fe, Ni and Ru coordinately linked to three 5-carboxyl-2,2'-bipyridine polypeptide binding ligands, each of which polypeptide binding ligands is independently covalently bonded to a linear amphiphilic peptide having the formula, reading from left to right in the direction from the N-terminus to the C-terminus:

-Gly-Glu-Leu-Ala-Glu-Gln-Lys-Leu-Glu-Gln-Ala-Leu-Gln-Lys-Leu-Ala- (SEQ ID NO:18).

5. The metallopolypeptide according to claim 4 wherein the polyvalent metal ion is Ru.

* * * * *

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

Gly Leu Ala Gln Lys Leu Leu Glu Ala Leu Gln Lys Ala Leu Ala
    1             5                  10              15

( 2 ) INFORMATION FOR SEQ ID NO:2:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( i x ) FEATURE:
    ( A ) NAME/KEY: Modified-site
    ( B ) LOCATION: 1
    ( C ) OTHER INFORMATION: /label =Ac
        / note ="Ac represents
        an acetylated amino
        terminus"

( i x ) FEATURE:
    ( A ) NAME/KEY: Modified-site
    ( B ) LOCATION: 17
    ( C ) OTHER INFORMATION: /label =CONH$_2$
        / note ="CONH$_2$ represents
        an amidated carboxyl
        terminus"

( x i ) SEQUENCE DESCRIPTION: SEQ ID NO:2:

Ala Glu Ala Ala Ala Lys Glu Ala Ala Ala Lys Cys Ala Ala Ala His
1            5                    10                15

Ala ( 2 ) INFORMATION FOR SEQ ID NO:3:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( C ) OTHER INFORMATION: /label =Ac
            / note ="Ac represents
            an acetylated amino
            terminus"

( i x ) FEATURE:
        ( A ) NAME/KEY: Modified-site
        ( B ) LOCATION: 17
        ( C ) OTHER INFORMATION: /label =CONH$_2$
            / note ="CONH$_2$ represents
            an amidated carboxyl
            terminus"

( x i ) SEQUENCE DESCRIPTION: SEQ ID NO:3:

Ala Glu Ala Ala Ala Lys Glu Ala Ala Ala Lys His Ala Ala Ala His
1            5                    10                15

Ala ( 2 ) INFORMATION FOR SEQ ID NO:4:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( C ) OTHER INFORMATION: /label =Ac
            / note ="Ac represents
            an acetylated amino
            terminus"

( i x ) FEATURE:
        ( A ) NAME/KEY: Modified-site
        ( B ) LOCATION: 17
        ( C ) OTHER INFORMATION: /label =CONH$_2$
            / note ="CONH$_2$ represents
            an amidated carboxyl
            terminus"

( x i ) SEQUENCE DESCRIPTION: SEQ ID NO:4:

Ala Glu Ala Ala Ala Lys His Ala Ala Ala His Glu Ala Ala Ala Lys
1               5                   10                  15

Ala ( 2 ) INFORMATION FOR SEQ ID NO:5:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( C ) OTHER INFORMATION: /label =Ac
            / note ="Ac represents
            an acetylated amino
            terminus"

( i x ) FEATURE:
        ( A ) NAME/KEY: Modified-site
        ( B ) LOCATION: 17
        ( C ) OTHER INFORMATION: /label =$CONH_2$
            / note ="$CONH_2$ represents
            an amidated carboxyl
            terminus"

( x i ) SEQUENCE DESCRIPTION: SEQ ID NO:5:

Ala His Ala Ala Ala His Glu Ala Ala Ala Lys Glu Ala Ala Ala Lys
1               5                   10                  15

Ala ( 2 ) INFORMATION FOR SEQ ID NO:6:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( C ) OTHER INFORMATION: /label =Ac
            / note ="Ac represents
            an acetylated amino
            terminus"

( i x ) FEATURE:
        ( A ) NAME/KEY: Modified-site
        ( B ) LOCATION: 17
        ( C ) OTHER INFORMATION: /label =$CONH_2$
            / note ="$CONH_2$ represents
            an amidated carboxyl
            terminus"

( x i ) SEQUENCE DESCRIPTION: SEQ ID NO:6:

Ala Cys Ala Ala Ala His Glu Ala Ala Ala Lys Glu Ala Ala Ala Lys
1               5                   10                  15

Ala ( 2 ) INFORMATION FOR SEQ ID NO:7:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: peptide ( i x ) FEATURE:
    ( A ) NAME/KEY: Modified-site
    ( B ) LOCATION: 1
    ( C ) OTHER INFORMATION: /label =Ac
        / note ="Ac represents
        an acetylated amino
        terminus"

( i x ) FEATURE:
    ( A ) NAME/KEY: Modified-site
    ( B ) LOCATION: 19
    ( C ) OTHER INFORMATION: /label =CONH$_2$
        / note ="CONH$_2$ represents
        an amidated carboxyl
        terminus"

( x i ) SEQUENCE DESCRIPTION: SEQ ID NO:7:

Ala Ala His Ala Leu Glu His Gln Ala Lys Ala Leu Lys Glu Ala Ala
1               5                   10                  15

Gln Lys Ala ( 2 ) INFORMATION FOR SEQ ID NO:8:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( C ) OTHER INFORMATION: /label =Ac
            / note ="Ac represents
            an acetylated amino
            terminus"

( i x ) FEATURE:
        ( A ) NAME/KEY: Modified-site
        ( B ) LOCATION: 19
        ( C ) OTHER INFORMATION: /label =CONH$_2$
            / note ="CONH$_2$ represents
            an amidated carboxyl
            terminus"

( x i ) SEQUENCE DESCRIPTION: SEQ ID NO:8:

Ala Ala Cys Ala Leu Glu His Gln Ala Lys Ala Leu Lys Glu Ala Ala
1               5                   10                  15

Gln Lys Ala ( 2 ) INFORMATION FOR SEQ ID NO:9:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( C ) OTHER INFORMATION: /label =Ac
            / note ="Ac represents
            an acetylated amino
            terminus"

( i x ) FEATURE:
        ( A ) NAME/KEY: Modified-site
        ( B ) LOCATION: 19
        ( C ) OTHER INFORMATION: /label =CONH$_2$
            / note ="CONH$_2$ represents
            an amidated carboxyl
            terminus"

( x i ) SEQUENCE DESCRIPTION: SEQ ID NO:9:

Ala Ala His Ala Leu Glu Cys Gln Ala Lys Ala Leu Lys Glu Ala Ala
1               5                   10                  15

Gln Lys Ala ( 2 ) INFORMATION FOR SEQ ID NO:10:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( C ) OTHER INFORMATION: /label =Ac
            / note ="Ac represents
            an acetylated amino
            terminus"

( i x ) FEATURE:
        ( A ) NAME/KEY: Modified-site
        ( B ) LOCATION: 3
        ( C ) OTHER INFORMATION: /label =Xaa
            / note ="Xaa represents
            a non- naturally-occurring
            amino acid with the chemical
            formula: $NH_2CH(R)—CO_2H$, where
            $R=(CH_2)_n—NHC(O)—5-\{2,2'$-bi-
            pyridine$\}$, and n=3."

( i x ) FEATURE:
        ( A ) NAME/KEY: Modified-site
        ( B ) LOCATION: 7
        ( C ) OTHER INFORMATION: /label =Xaa
            / note ="Xaa represents
            a non- naturally-occurring
            amino acid with the chemical
            formula: $NH_2CH(R)—CO_2H$, where
            $R=(CH_2)_n—NHC(O)—5-\{2,2'$-bi-
            pyridine$\}$, and n=3."

( i x ) FEATURE:
        ( A ) NAME/KEY: Modified-site
        ( B ) LOCATION: 19
        ( C ) OTHER INFORMATION: /label =$CONH_2$
            / note ="$CONH_2$ represents
            an amidated carboxyl
            terminus"

( x i ) SEQUENCE DESCRIPTION: SEQ ID NO:10:

Ala Ala Xaa Ala Leu Glu Xaa Gln Ala Lys Ala Leu Lys Glu Ala Ala
1               5                   10                  15

Gln Lys Ala ( 2 ) INFORMATION FOR SEQ ID NO:11:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( C ) OTHER INFORMATION: /label =Ac
            / note ="Ac represents
            an acetylated amino
            terminus"

( i x ) FEATURE:

(A) NAME/KEY: Modified-site
(B) LOCATION: 3
(C) OTHER INFORMATION: /label =Xaa
/ note ="Xaa represents
a non- naturally-occurring
amino acid with the chemical
formula: $NH_2CH(R)-CO_2H$, where
$R=(CH_2)_n-N(CH_2CO_2H)_2$, and $n=3$."

(ix) FEATURE:
(A) NAME/KEY: Modified-site
(B) LOCATION: 7
(C) OTHER INFORMATION: /label =Xaa
/ note ="Xaa represents
a non- naturally-occurring
amino acid with the chemical
formula: $NH_2CH(R)-CO_2H$, where
$R=(CH_2)_n-N(CH_2CO_2H)_2$, and n=3."

(ix) FEATURE:
(A) NAME/KEY: Modified-site
(B) LOCATION: 19
(C) OTHER INFORMATION: /label =$CONH_2$
/ note ="$CONH_2$ represents
an amidated carboxyl
terminus"

(xi) SEQUENCE DESCRIPTION: SEQ ID NO:11:

Ala Ala Xaa Ala Leu Glu Xaa Gln Ala Lys Ala Leu Lys Glu Ala Ala
1               5                   10                  15

Gln Lys Ala (2) INFORMATION FOR SEQ ID NO:12:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1
(C) OTHER INFORMATION: /label =Ac
/ note ="Ac represents
an acetylated amino
terminus"

(ix) FEATURE:
(A) NAME/KEY: Modified-site
(B) LOCATION: 14
(C) OTHER INFORMATION: /label =$CONH_2$
/ note ="$CONH_2$ represents
an amidated carboxyl
terminus"

(xi) SEQUENCE DESCRIPTION: SEQ ID NO:12:

His Leu Ser Val Val His Pro Gly His Thr Tyr Ile Gln His
1               5                   10

(2) INFORMATION FOR SEQ ID NO:13:

(i) SEQUENCE CHARACTERISTICS:
(A) LENGTH: 14 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1
(C) OTHER INFORMATION: /label =Ac
/ note ="Ac represents
an acetylated amino
terminus"

( i x ) FEATURE:
    ( A ) NAME/KEY: Modified-site
    ( B ) LOCATION: 14
    ( C ) OTHER INFORMATION: /label =CONH$_2$
      / note ="CONH$_2$ represents
      an amidated carboxyl
      terminus"

( x i ) SEQUENCE DESCRIPTION: SEQ ID NO:13:

```
His Leu Ser Val Val His Pro Gly His Thr Tyr Ile Gln Cys
1               5                   10
```

( 2 ) INFORMATION FOR SEQ ID NO:14:

( i ) SEQUENCE CHARACTERISTICS:
      ( A ) LENGTH: 14 amino acids
      ( B ) TYPE: amino acid
      ( D ) TOPOLOGY: linear ( i i ) MOLECULE TYPE: peptide ( i x ) FEATURE:
      ( A ) NAME/KEY: Modified-site
      ( B ) LOCATION: 1
      ( C ) OTHER INFORMATION: /label =Ac
        / note ="Ac represents
        an acetylated amino
        terminus"

( i x ) FEATURE:
      ( A ) NAME/KEY: Modified-site
      ( B ) LOCATION: 14
      ( C ) OTHER INFORMATION: /label =CONH$_2$
        / note ="CONH$_2$ represents
        an amidated carboxyl
        terminus"

( x i ) SEQUENCE DESCRIPTION: SEQ ID NO:14:

```
Cys Leu Ser Val Val His Pro Gly His Thr Tyr Ile Gln Cys
1               5                   10
```

( 2 ) INFORMATION FOR SEQ ID NO:15:

( i ) SEQUENCE CHARACTERISTICS:
      ( A ) LENGTH: 14 amino acids
      ( B ) TYPE: amino acid
      ( D ) TOPOLOGY: linear ( i i ) MOLECULE TYPE: peptide ( i x ) FEATURE:
      ( A ) NAME/KEY: Modified-site
      ( B ) LOCATION: 1
      ( C ) OTHER INFORMATION: /label =Ac
        / note ="Ac represents
        an acetylated amino
        terminus"

( i x ) FEATURE:
      ( A ) NAME/KEY: Modified-site
      ( B ) LOCATION: 14
      ( C ) OTHER INFORMATION: /label =CONH$_2$
        / note ="CONH$_2$ represents
        an amidated carboxyl
        terminus"

( x i ) SEQUENCE DESCRIPTION: SEQ ID NO:15:

```
Cys Leu Ser Val Val Cys Pro Gly His Thr Tyr Ile Gln Cys
1               5                   10
```

( 2 ) INFORMATION FOR SEQ ID NO:16:

( i ) SEQUENCE CHARACTERISTICS:
      ( A ) LENGTH: 14 amino acids
      ( B ) TYPE: amino acid (D) TOPOLOGY: linear (ii) MOLECULE TYPE: peptide (ix) FEATURE:
            (A) NAME/KEY: Modified-site
            (B) LOCATION: 1
            (C) OTHER INFORMATION: /label =Ac
                    / note ="Ac represents
                    an acetylated amino
                    terminus"

(ix) FEATURE:
            (A) NAME/KEY: Modified-site
            (B) LOCATION: 14
            (C) OTHER INFORMATION: /label =CONH$_2$
                    / note ="CONH$_2$ represents
                    an amidated carboxyl
                    terminus"

(xi) SEQUENCE DESCRIPTION: SEQ ID NO:16:

Cys Leu Ser Val Val Cys Pro Gly Cys Thr Tyr Ile Gln Cys
1               5                   10

(2) INFORMATION FOR SEQ ID NO:17:

(i) SEQUENCE CHARACTERISTICS:
            (A) LENGTH: 22 amino acids
            (B) TYPE: amino acid
            (D) TOPOLOGY: linear (ii) MOLECULE TYPE: peptide (xi) FEATURE:
            (A) NAME/KEY: Modified-site
            (B) LOCATION: 22
            (C) OTHER INFORMATION: /label =Xaa
                    / note ="Xaa is Orn"

(xi) SEQUENCE DESCRIPTION: SEQ ID NO:17:

Gly Ala Leu Ala Ile Phe Leu Leu Ile Ala Leu Phe Ala Leu Leu Ala
1               5                   10                  15
Ile Phe Leu Leu Ala Xaa
                20

(2) INFORMATION FOR SEQ ID NO:18:

(i) SEQUENCE CHARACTERISTICS:
            (A) LENGTH: 16 amino acids
            (B) TYPE: amino acid
            (D) TOPOLOGY: linear (ii) MOLECULE TYPE: peptide (xi) SEQUENCE DESCRIPTION: SEQ ID NO:18:

Gly Glu Leu Ala Glu Gln Lys Leu Glu Gln Ala Leu Gln Lys Leu Ala
1               5                   10                  15

(2) INFORMATION FOR SEQ ID NO:19:

(i) SEQUENCE CHARACTERISTICS:
            (A) LENGTH: 14 amino acids
            (B) TYPE: amino acid
            (D) TOPOLOGY: linear (ii) MOLECULE TYPE: peptide (xi) SEQUENCE DESCRIPTION: SEQ ID NO:19:

Cys Leu Ser Val Val His Pro Gly His Thr Tyr Ile Gln Cys
1               5                   10

(2) INFORMATION FOR SEQ ID NO:20:

( i ) SEQUENCE CHARACTERISTICS:
  ( A ) LENGTH: 12 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:20:

Val Asn Val Lys His Gly Ser His Asn Val Lys Val
 1           5                   10